United States Patent
Dax et al.

(10) Patent No.: US 6,841,552 B1
(45) Date of Patent: Jan. 11, 2005

(54) 3A,4,5,9B-TETRAHYDRO-1H-BENZ[E]INDOL-2-YL AMINE-DERIVED NEUROPEPTIDE Y RECEPTORS LIGANDS USEFUL IN THE TREATMENT OF OBESITY AND OTHER DISORDERS

(75) Inventors: Scott Dax, Landenberg, PA (US); James McNally, Souderton, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/552,969

(22) Filed: Apr. 20, 2000

Related U.S. Application Data

(60) Provisional application No. 60/132,660, filed on May 5, 1999.

(51) Int. Cl.[7] .................... C07D 211/30; C07D 401/00; C07D 209/56; C07D 403/00; A61K 31/495
(52) U.S. Cl. ................. 514/254.08; 546/190; 546/200; 548/427; 548/305.1; 514/411; 514/387; 544/372
(58) Field of Search ................................ 546/190, 200; 548/427, 305.1; 514/411, 387, 254.08; 544/372

(56) References Cited

FOREIGN PATENT DOCUMENTS

| WO | 97 19682 A | 6/1997 |
|----|------------|--------|
| WO | 97 20823 A | 6/1997 |
| WO | 98 35957 A | 8/1998 |
| WO | 99 55667 A | 11/1999 |
| WO | 00 20376 A | 4/2000 |

OTHER PUBLICATIONS

McNally et al. N–(Sulfonamido)alkyl[tetrahydro–1H–benzo[e]indol–2–yl]amines: Potent Antagonists of Human Neuropeptide Y Y5 Receptor Mar. 2000.*

McNall, James J. et al: "N– (Sulfonamidoalkyl)(tetrahydro–1H–benz'e!indol–2–yl) amines: potent antagonists of human neuropeptide Y Y5 receptor" Bioorg. Med. Chen. Lett. (2000), 10(3), 213–216 XP004188819 the whole document

* cited by examiner

Primary Examiner—Richard L. Raymond
Assistant Examiner—Hong Liu

(57) ABSTRACT

Compounds of the formula:

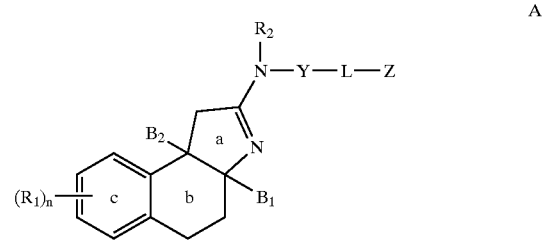

are disclosed as ligands for neuropeptide Y receptors and as such are useful in the treatment of obesity and disorders of the central nervous system.

17 Claims, No Drawings

3A,4,5,9B-TETRAHYDRO-1H-BENZ[E]INDOL-2-YL AMINE-DERIVED NEUROPEPTIDE Y RECEPTORS LIGANDS USEFUL IN THE TREATMENT OF OBESITY AND OTHER DISORDERS

This is a non-provisional of Application Ser. No. 60/132,660, filed May 5, 1999.

FIELD OF THE INVENTION

This invention relates to a series of 3a,4,5,9b-tetrahydro-1H-benz[e]indol-2-yl amine derivatives, pharmaceutical compositions containing them and intermediates used in their preparation. The compounds of the invention are ligands for the neuropeptide Y Y5 (NPY5) receptor, a receptor which is associated with a number of central nervous system disorders and affective conditions.

BACKGROUND OF THE INVENTION

Regulation and function of the mammalian central nervous system is governed by a series of interdependent receptors, neurons, neurotransmitters, and proteins. The neurons play a vital role in this system for, when externally or internally stimulated, they react by releasing neurotransmitters that bind to specific proteins. Common examples of endogenous small molecule neurotransmitters such as acetylcholine, adrenaline, norepinephrine, dopamine, serotonin, glutamate, and gamma-aminobutyric acid are well known, as are the specific receptors that recognize these compounds as ligands ("The Biochemical Basis of Neuropharmacology", Sixth Edition, Cooper, J. R.; Bloom, F. E.; Roth, R. H. Eds., Oxford University Press, New York, N.Y. 1991).

In addition to the endogenous small molecule neurotransmitters, there is increasing evidence that neuropeptides play an integral role in neuronal operations. Neuropeptides are now believed to be co-localized with perhaps more than one-half of the 100 billion neurons of the human central nervous system. In addition to humans, neuropeptides have been discovered in a number of animal species. In some instances the composition of these peptides is remarkably homogenous among species. This finding suggests that the function of neuropeptides is vital and has been impervious to evolutionary changes. Furthermore, neuropeptides, unlike small molecule neurotransmitters, are typically synthesized by the neuronal ribosome. In some cases, the active neuropeptides are produced as part of a larger protein which is enzymatically processed to yield the active substance. Based upon these differences, compared to small molecule neurotransmitters, neuropeptide-based strategies may offer novel therapies for CNS diseases and disorders. Specifically, agents that affect the binding of neuropeptides to their respective receptors or ameliorate responses that are mediated by neuropeptides are potentially useful in therapies for diseases associated with neuropeptides.

There are a number of afflictions that are associated with the complex interdependent system of receptors and ligands within the central nervous system; these include neurodegenerative diseases, affective disorders such as anxiety, depression, pain and schizophrenia, and affective conditions that include a metabolic component, namely obesity. Such conditions, disorders and diseases have been treated with small molecules and peptides which modulate neuronal responses to endogenous neurotransmitters.

One example of the class of neuropeptides is neuropeptide Y (NPY). NPY was first isolated from porcine brain (Tatemoto, K. et al. *Nature* 1982, 296, 659) and was shown to be structurally similar to other members of the pancreatic polypeptide (PP) family such as peptide YY, which is primarily synthesized by endocrine cells in the gut, and pancreatic polypeptide, which is synthesized by the pancreas. Neuropeptide Y is a single peptide protein that consists of thirty-six amino acids containing an amidated C-terminus. Like other members of the pancreatic polypeptide family, NPY has a distinctive conformation that consists of an N-terminal polyproline helical region and an amphiphilic α-helix joined by a characteristic PP-fold (Vladimir, S. et. Al. *Biochemistry* 1990, 20, 4509). Furthermore, NPY sequences from a number of animal species have been elucidated and all show a high degree of amino acid homology to the human protein (>94% in rat, dog, rabbit, pig, cow, sheep) (see Larhammar, D. in "The Biology of Neuropeptide Y and Related Peptides", Colmers, W. F. and Wahlestedt, C. Eds., Humana Press, Totowa, N.J. 1993).

Endogenous receptor proteins that bind NPY and related peptides as ligands have been identified and distinguished, and several such proteins have been cloned and expressed. Six different receptor subtypes [Y1, Y2, Y3, Y4(PP), Y5, Y6 (formerly designated as a Y5 receptor)] are recognized today based upon binding profile, pharmacology and/or composition if identity is known (Wahlestedt, C. et. al. *Ann. NY Acad. Sci.* 1990, 611, 7; Larhammar, D. et. al. *J. Biol. Chem.* 1992, 267, 10935; Wahlestedt, C. et. al. *Regul. Pept.* 1986, 13, 307; Fuhlendorff, J. U. et. al. *Proc. Natl. Acad. Sci. USA* 1990, 87, 182; Grundemar, L. et. al. *J. Pharmacol. Exp. Ther.* 1991, 258, 633; Laburthe, M. et. al. *Endocrinology* 1986, 118, 1910; Castan, I. et. al. *Endocrinology* 1992, 131, 1970; Gerald, C. et. al. *Nature* 1996, 382, 168; Weinberg, D. H. et. al. *Journal of Biological Chemistry* 1996, 271, 16435; Gehlert, D. et. al. *Current Pharmaceutical Design* 1995, 1, 295; Lundberg, J. M. et. al. *Trends in Pharmaceutical Sciences* 1996, 17, 301). Most and perhaps all NPY receptor proteins belong to the family of so-called G-protein coupled receptors (GPCRs). The neuropeptide Y5 receptor, a putative GPCR, is negatively coupled to cellular cyclic adenosine monophosphate (cAMP) levels via the action of adenylate cyclase (Gerald, C. et. al. *Nature* 1996, 382, 168; Gerald, C. et. al. PCT WO 96/16542). For example, NPY inhibits forskolin-stimulated cAMP production/levels in a neuroblastoma cell line. A Y5 ligand that mimics NPY in this fashion is an agonist whereas one that competitively reverses the NPY inhibition of forskolin-stimulated cAMP production is an antagonist.

Neuropeptide Y itself is the archetypal substrate for the NPY receptors and its binding can elicit a variety of pharmacological and biological effects in vitro and in vivo. When administered to the brain of live animals (intracerebroventricularly (icv) or into the amygdala), NPY produces anxiolytic effects in established animal models of anxiety such as the elevated plus-maze, Vogel punished drinking and Geller-Seifter's bar-pressing conflict paradigms (Heilig, M. et. al. *Psychopharmacology* 1989, 98, 524; Heilig, M. et. al. *Reg. Peptides* 1992, 41, 61; Heilig, M. et. al. *Neuropsycho-pharmacology* 1993, 8, 357). Thus compounds that mimic NPY are postulated to be useful for the treatment of anxiolytic disorders.

The immunoreactivity of neuropeptide Y is notably decreased in the cerebrospinal fluid of patients with major depression and those of suicide victims (Widdowson, P. S. et. al. *Journal of Neurochemistry* 1992, 59, 73), and rats treated with tricyclic antidepressants display significant increases of NPY relative to a control group (Heilig, M. et.

al. *European Journal of Pharmacology* 1988, 147, 465). These findings suggest that an inadequate NPY response may play a role in some depressive illnesses, and that compounds that regulate the NPY-ergic system may be useful for the treatment of depression.

Neuropeptide Y improves memory and performance scores in animal models of learning (Flood, J. F. et. al. *Brain Research* 1987, 421, 280) and therefore may serve as a cognition enhancer for the treatment of neurodegenerative diseases such as Alzheimer's Disease (AD) as well as AIDS-related and senile dementia.

Elevated plasma levels of NPY are present in animals and humans experiencing episodes of high sympathetic nerve activity such as surgery, newborn delivery and hemorrhage (Morris, M. J. et. al. *Journal of Autonomic Nervous System* 1986, 17, 143). Thus chemical substances that alter the NPY-ergic system may be useful for alleviating the condition of stress.

Neuropeptide Y also mediates endocrine functions such as the release of luteinizing hormone (LH) in rodents (Kalra, S. P. et. al. *Frontiers in Neuroendrocrinology* 1992, 13, 1). Since LH is vital for mammalian ovulation, a compound that mimics the action of NPY could be useful for the treatment of infertility, particularly in women with so-called luteal phase defects.

Neuropeptide Y is a powerful stimulant of food intake; as little as one-billionth of a gram, when injected directly into the CNS, causes satiated rats to overeat (Clark, J. T. et. al. *Endocrinology* 1984, 115, 427; Levine, A. S. et. al. *Peptides* 1984, 5, 1025; Stanley, B. G. et. al. *Life Sci.* 1984, 35, 2635; Stanley, B. G. et. al. *Proc. Nat. Acad. Sci. USA* 1985, 82, 3940). Thus NPY is orexigenic in rodents but not anxiogenic when given intracerebroventricularly and so antagonism of neuropeptide receptors may be useful for the treatment of eating disorders such as obesity, anorexia nervosa and bulimia nervosa.

In recent years, a variety of potent, structurally distinct small molecule Y1 antagonists has been discovered and developed (Hipskind, P. A. et. al. *Annu. Rep. Med. Chem.* 1996, 31, 1–10; Rudolf, K. et. al. *Eur. J. Pharmacol.* 1994, 271, R11; Serradeil-Le Gal, C. et. al. *FEBS Lett.* 1995, 362, 192; Wright, J. et. al. *Bioorg. Med. Chem. Lett.* 1996, 6, 1809; Poindexter, G. S. et. al. U.S. Pat. No. 5,668,151; Peterson, J. M. et. al. WO9614307 (1996)). However, despite claims of activity in rodent models of feeding, it is unclear if inhibition of a feeding response can be solely attributed to antagonism of the Y1 receptor.

Several landmark studies suggest that an "atypical Y1" receptor and/or the Y5 receptor, rather than the classic Y1 receptor, is responsible for invoking NPY-stimulated food consumption in animals. It has been shown that the NPY fragment $NPY_{2-36}$ is a potent inducer of feeding despite poor binding at the classic Y1 receptor (Stanley, B. G. et. al. *Peptides* 1992, 13, 581). Conversely, a potent and selective Y1 agonist has been reported to be inactive at stimulating feeding in animals (Kirby, D. A. et. al. *J. Med. Chem.* 1995, 38, 4579). More pertinent to the invention described herein, [D-Trp$^{32}$]NPY, a selective Y5 receptor activator has been reported to stimulate food intake when injected into the hypothalamus of rats (Gerald, C. et. al. Nature 1996, 362, 168). Since [D-Trp$^{32}$]NPY appears to be a full agonist of the Y5 receptor with no appreciable Y1 activity, the Y5 receptor is hypothesized to be responsible for the feeding response. Accordingly compounds that antagonize the Y5 receptor should be effective in inhibiting food intake, particularly that stimulated by NPY.

Certain arylsulfonamides that act as Y5 antagonists are known in the prior art. In PCT WO 97/19682, aryl sulfonamides and sulfamides derived from arylalkylamines are described as Y5 antagonists and are reported to reduce food consumption in animals. In PCT WO 97/20820, PCT WO 97/20822 and PCT WO 97/20823, sulfonamides containing heterocyclic systems such as quinazolin-2,4-diazirines, are likewise claimed as Y5 antagonists and reported to reduce feeding. In WO 98/35957, various amide derivatives, including those that contain a benzimidazolinone group are claimed to be neuropeptide Y receptor antagonists. However, none of these compounds known in the prior art contain the amidine ring system present in the compounds of this invention. The cyclic amidino sulfonamides and amidino benzimidazolinones and amidino arylpiperazines described in this application are novel molecular entities that may have binding motifs that are different from Y5 receptor ligands that have been disclosed in prior publications, and yet bind to a similar region of the Y5 receptor. In addition to exhibiting an affinity for the neuropeptide Y5 receptor, the compounds of this invention may also produce pharmacological and biological responses that are, in part or wholly, due to activation or antagonism of other Y receptor subtypes (e.g., Y1, Y2, Y4).

SUMMARY OF THE INVENTION

The present invention is related to compounds of formula A

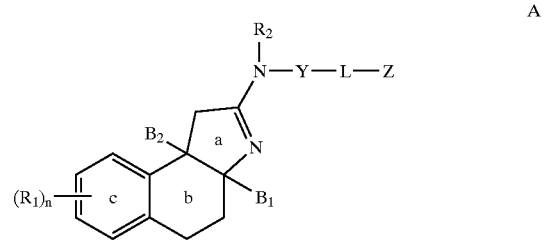

in which

R$_1$ is independently selected from the group consisting of hydrogen; hydroxy; halo; C$_{1-8}$alkyl; C$_{1-8}$alkoxy; substituted C$_{1-8}$ alkyl wherein the substituent is selected from halo, such as chloro, bromo, fluoro and iodo; substituted C$_{1-8}$ alkoxy wherein the substituent is selected from halo, such as chloro, bromo, fluoro and iodo; trifluoroalkyl; C$_{1-8}$ alkylthio and substituted C$_{1-8}$alkylthio wherein the substituent is selected from halo, such as chloro, bromo, fluoro and iodo, trifluoroalkyl and C$_{1-8}$alkoxy; C$_{3-8}$cycloalkyl; C$_{3-8}$cycloalkyloxy; nitro; amino; C$_{1-6}$alkylamino; C$_{1-8}$dialkylamino; C$_{4-8}$cycloalkylamino; cyano; carboxy; C$_{1-5}$alkylcarbonyloxy; C$_{1-5}$alkoxycarbonyloxy; formyl; carbamoyl; phenyl and substituted phenyl wherein the substitutent is selected from halo, hydroxyl, nitro, amino and cyano;

n is 0–2;

B$_2$ is selected from the group consisting of hydrogen; C$_{1-5}$alkyl; substituted C$_{1-5}$alkyl wherein the substituent is halo;

B$_2$ may have either a cis- or trans-stereochemical orientation with respect to B$_1$; both enantiomers of each diastereomeric set are part of the present invention;

Y is methylene (—CH$_2$—) or carbonyl (C=O)

L is selected from the group consisting of C$_{1-8}$alkylene; C$_{2-10}$alkenylene; C$_{2-10}$alkynylene; C$_{3-7}$cycloalkylene; C$_{3-7}$cycloalkylC$_{1-4}$alkylene; arylC$_{1-4}$alkylene; (N-methylene)piperidin-4-yl;

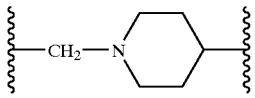

(N-methylene)piperazin-4-yl;

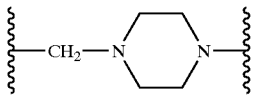

and (N-methylene)piperidin-4,4-diyl;

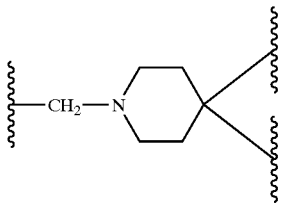

R$_2$ is independently selected from the group consisting of hydrogen; C$_{1-5}$alkyl; substituted C$_{1-5}$alkyl wherein the substituent is halo;

B$_1$ is hydrogen;
  B$_1$ may have either a cis- or trans-stereochemical orientation with respect to B$_2$; both enantiomers of each diastereomeric set are part of this invention.

Z is selected from the group consisting of:
  phenyl;

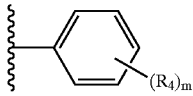

N-sulfonamido;

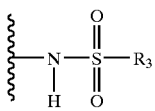

N-(aryl)sulfonamido;

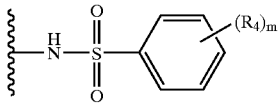

2,3-dihydro-2-oxo-1H-benzimidazol-1-yl;

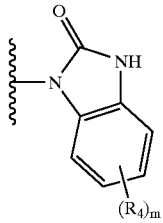

and 1-aryl-2,3-dihydro-4-oxo-imidazol-5,5-diyl;

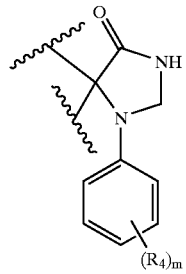

R$_3$ is independently selected from the group consisting of C$_{1-8}$alkyl; substituted C$_{1-8}$alkyl wherein the substituent is selected from C$_{1-8}$alkoxy and halo; cycloalkyl; substituted cycloalkyl wherein the substituent is selected from C$_{1-8}$alkoxy and halo; naphthyl; substituted naphthyl wherein the substituent is selected from halo, nitro, amino and cyano; heteroaryl wherein the heteroaryl group is selected from pyridyl, pyrimidyl, furyl, thienyl and imidazolyl; and substituted heteroaryl wherein the substituent is selected from halo, nitro, amino and cyano;

R$_4$ is independently selected from the group consisting of C$_{1-8}$alkyl; alkoxy; hydroxy; halogen; cyano, nitro; amino and alkylamino; substituted C$_{1-8}$alkyl wherein the substituent is halo;

m is 0–2;

and enantiomers, diastereomers, and pharmaceutically acceptable salts thereof,
  with the following provisions:
    when L is C$_{1-8}$alkylene, C$_{2-10}$alkenylene, C$_{2-10}$alkynylene, C$_{3-7}$cycloalkylene, C$_{3-7}$cycloalkylC$_{1-4}$alkylene, arylC$_{1-4}$alkylene or (N-methylene)piperidin-4-yl,
      then Z is phenyl, N-sulfonamido, N-(aryl)sulfonamido or 2,3-dihydro-2-oxo-1H-benzimidazol-1-yl;
    when L is (N-methylene)piperazin-4-yl,
      then Z is phenyl or naphthyl;
    and when L is (N-methylene)piperidin-4,4,-diyl;
    then Z is 1-aryl-2,3-dihydro-4-oxo-imidazol-5,5-diyl;

As used herein unless otherwise noted the terms "alkyl" and "alkoxy" whether used alone or as part of a substituent group, include straight and branched chains having 1–8 carbon atoms. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups. The term "aryl" is intended to include phenyl and naphthyl. The term "halo", unless otherwise indicated, includes bromo, chloro, fluoro and iodo. The term "cycloalkyl" is intended to include cycloalkyl groups having 3–7 carbon atoms. With reference to substituents, the term "independently" means that when more than one of such substituent is possible, such substituents may be the same or different from each other.

Those compounds of the present invention which contain a basic moiety can be converted to the corresponding acid addition salts by techniques known to those skilled in the art. Suitable acids which can be employed for this purpose include hydrochloric, hydrobromic, hydriodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. In general, the acid addition salts can be prepared by reacting the free base of compounds of formula A with the acid and isolating the salt.

Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

The daily dose of the active ingredient to be administered will depend on the age of the patient in need of such treatment, the particular condition to be treated and the manner of administration. Generally, an approximate daily dose of about 10 to about 500 mg is to be administered depending upon the mode of administration and the weight of the patient being treated. Determination of the optimum doses and frequency of administration for a particular disease state or disorder is within the experimental capabilities of those knowledgeable of the specific disease or disorder being treated.

For the treatment of disorders of the central nervous system, the pharmaceutical compositions described herein will typically contain from about 1 to about 1000 mg of the active ingredient per dosage; one or more doses per day may be administered. Determination of optimum doses and frequency of dosing for a particular disease state or disorder is within the experimental capabilities of those knowledgeable in the treatment of central nervous system disorders. The preferred dose range is from about 1–100 mg/kg.

As modulators of the NPY5 receptor, the compounds of Formula A are useful for treating feeding disorders such as obesity, anorexia nervosa and bulimia nervosa, and abnormal conditions such as epilepsy, depression, anxiety, sleeping disorders, dyspilipidimia, diabetes, hypertension, migraine, pain and sexual/reproductive disorders in which modulation of the NPY5 receptor may be useful. The compounds compete with the endogenous ligand PYY and possibly NPY and possibly non-endogenous ligands as well, and bind to the NPY5 receptor. In addition, the compounds demonstrate antagonist activity by antagonizing the action of NPY upon binding to the Y5 receptor.

The compounds described herein are ligands of the NPY5 receptor, but are not necessarily limited solely in their pharmacological or biological action due to binding to this or any neuropeptide, neurotransmitter or G-protein coupled receptor. For example, the described compounds may also undergo binding to dopamine or serotonin receptors. The compounds described herein are potentially useful in the regulation of metabolic and endocrine functions, particularly those associated with feeding, and as such, may be useful for the treatment of obesity. In addition, the compounds described herein are potentially useful for modulating other endocrine functions, particularly those controlled by the pituitary and hypothalamic glands, and therefore may be useful for the treatment of inovulation/infertility due to insufficient release of luteinizing hormone (LH).

The present invention comprises pharmaceutical compositions containing one or more of the compounds of Formula A.

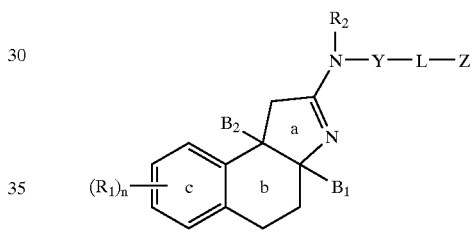

wherein $R_1$, $R_2$, $B_1$, $B_2$, Y, n, L and Z are defined as above. In addition, the present invention comprises intermediates used in the manufacture of these compounds.

Examples of preferred compounds of formula A include:

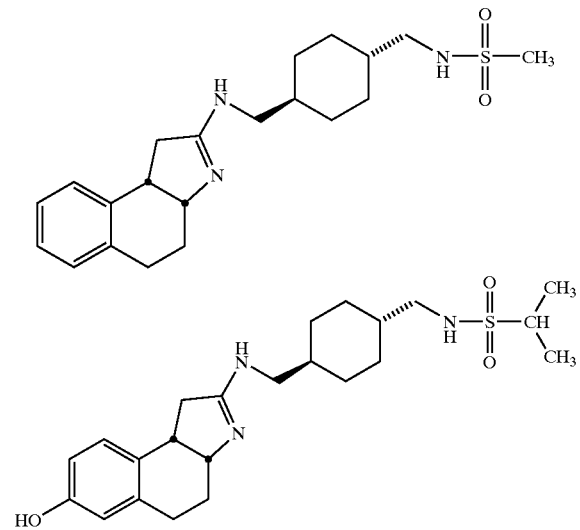

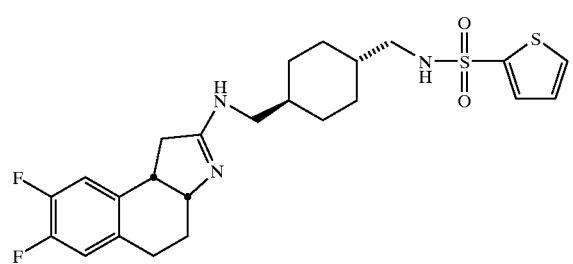
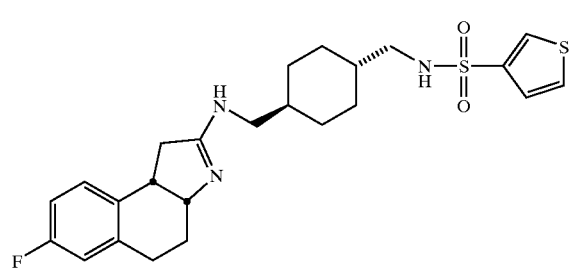
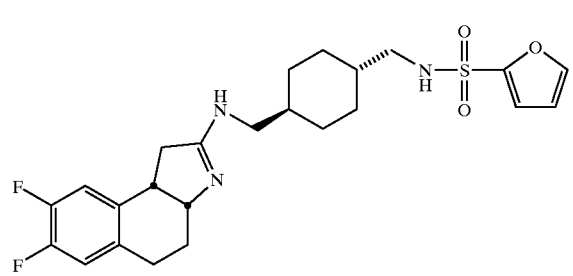
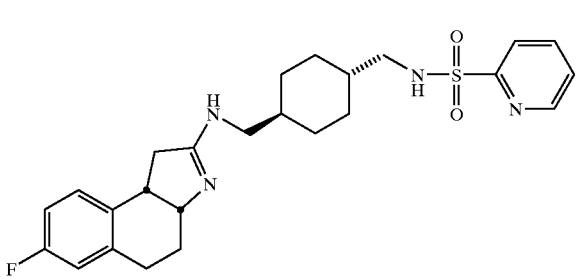
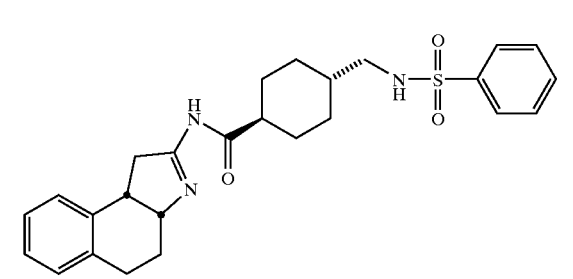
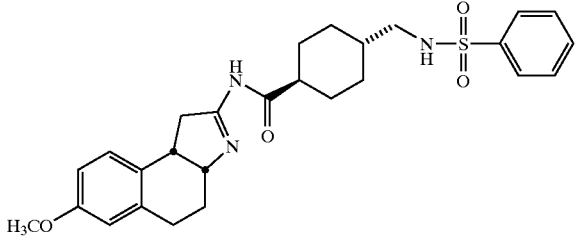
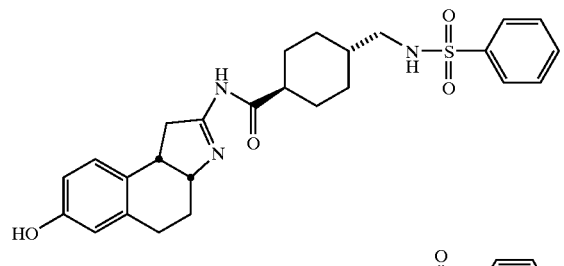
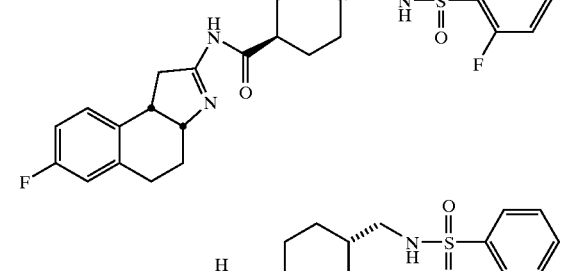
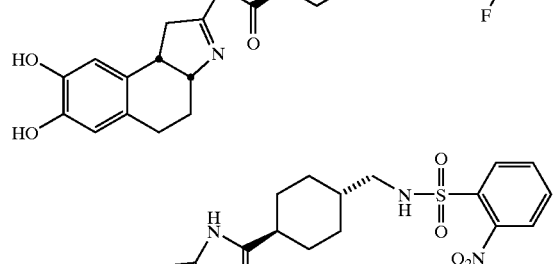
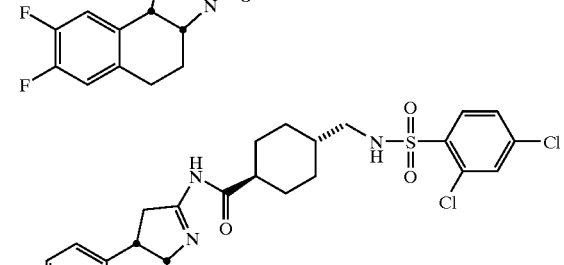
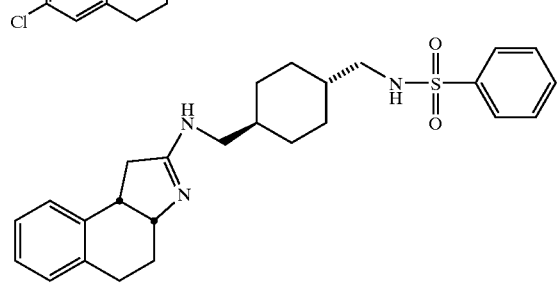
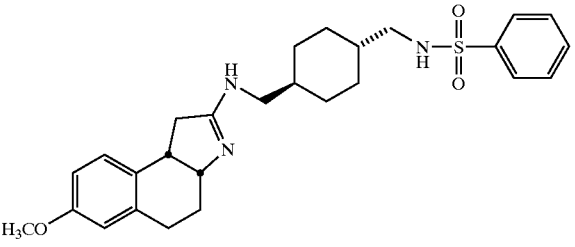

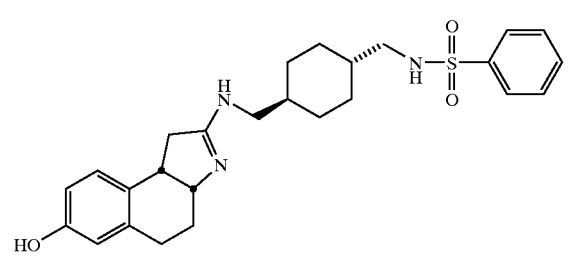
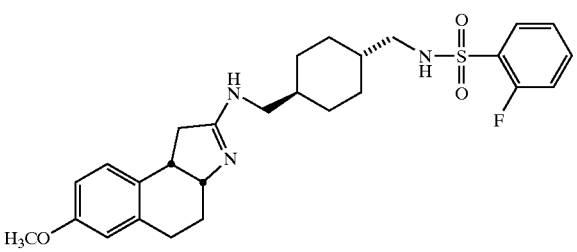
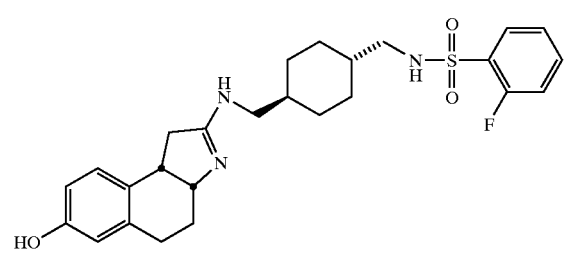
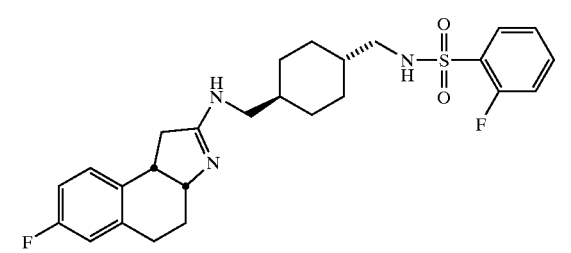
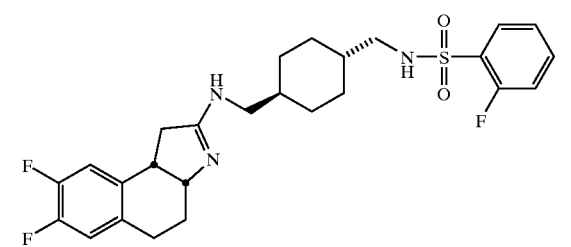
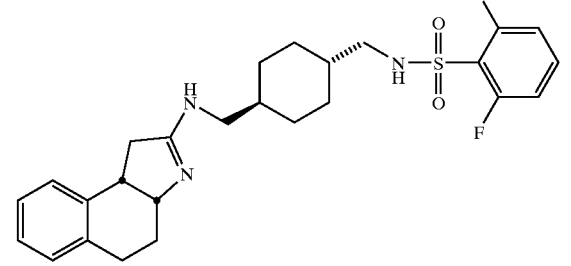
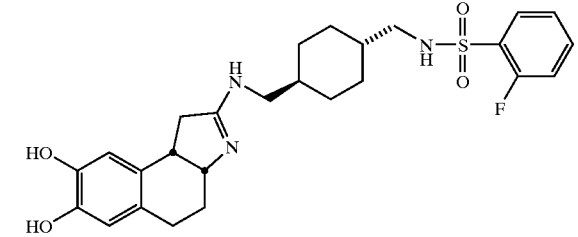
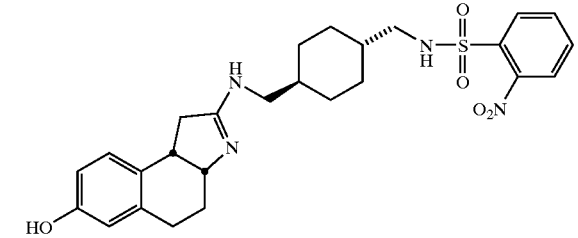
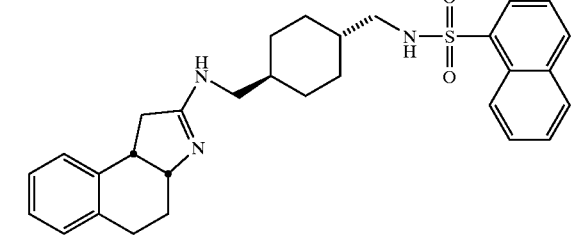
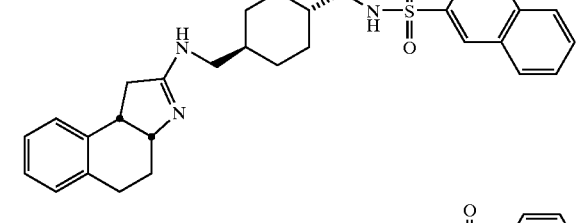
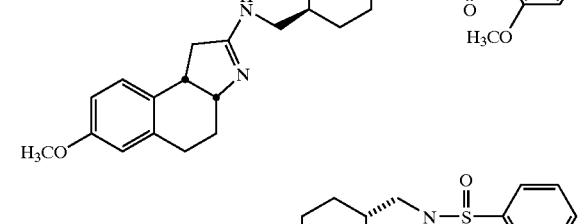
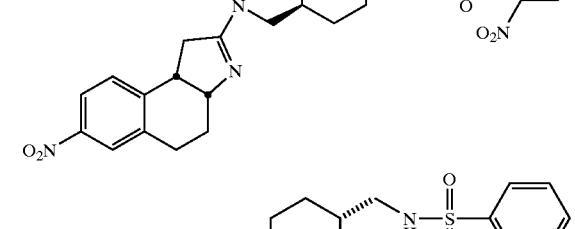

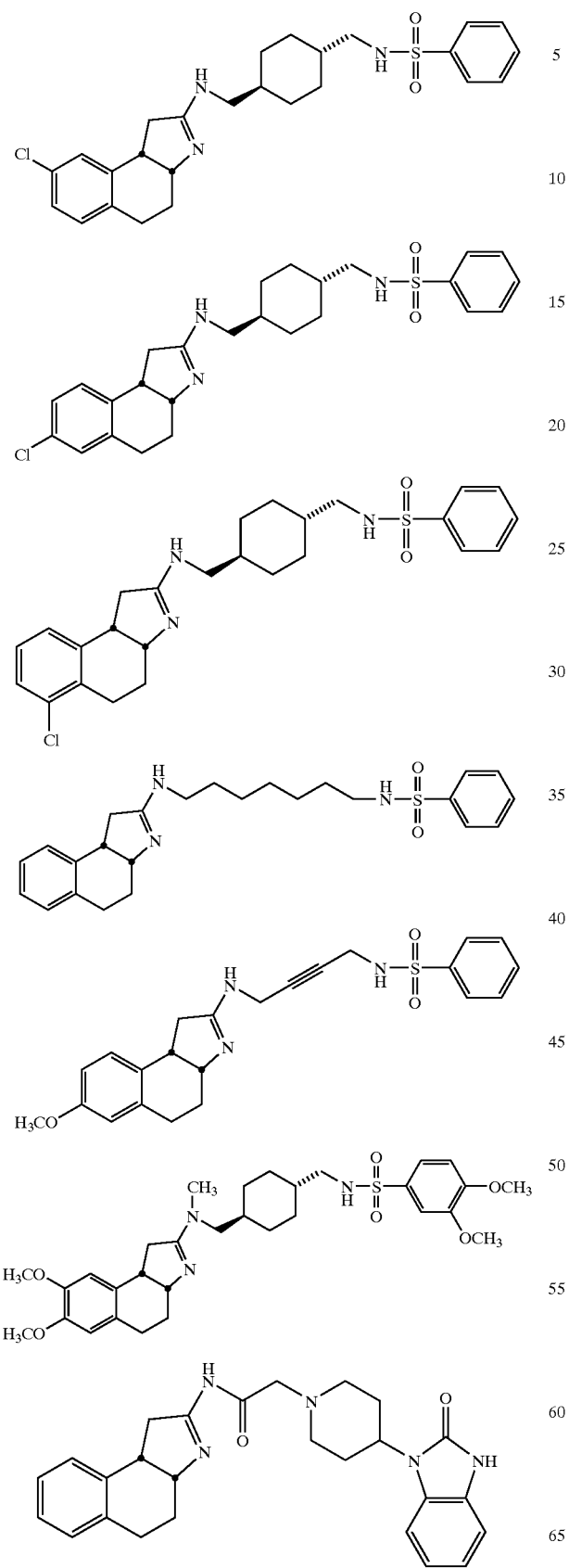
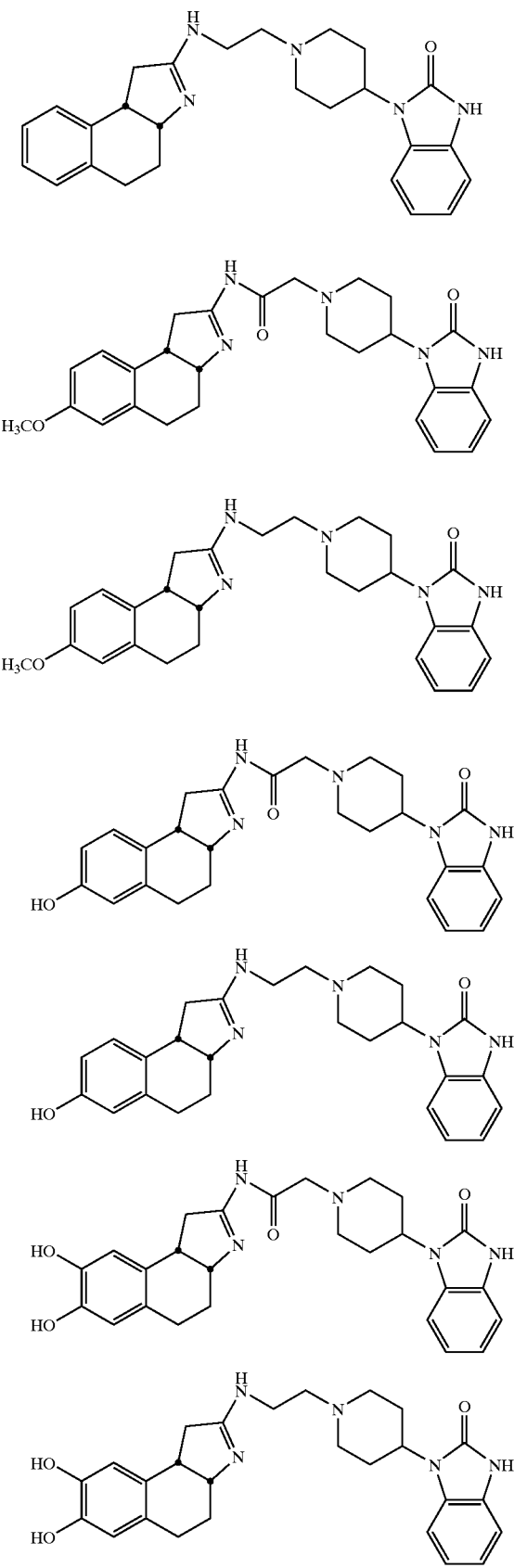

15
-continued

16
-continued

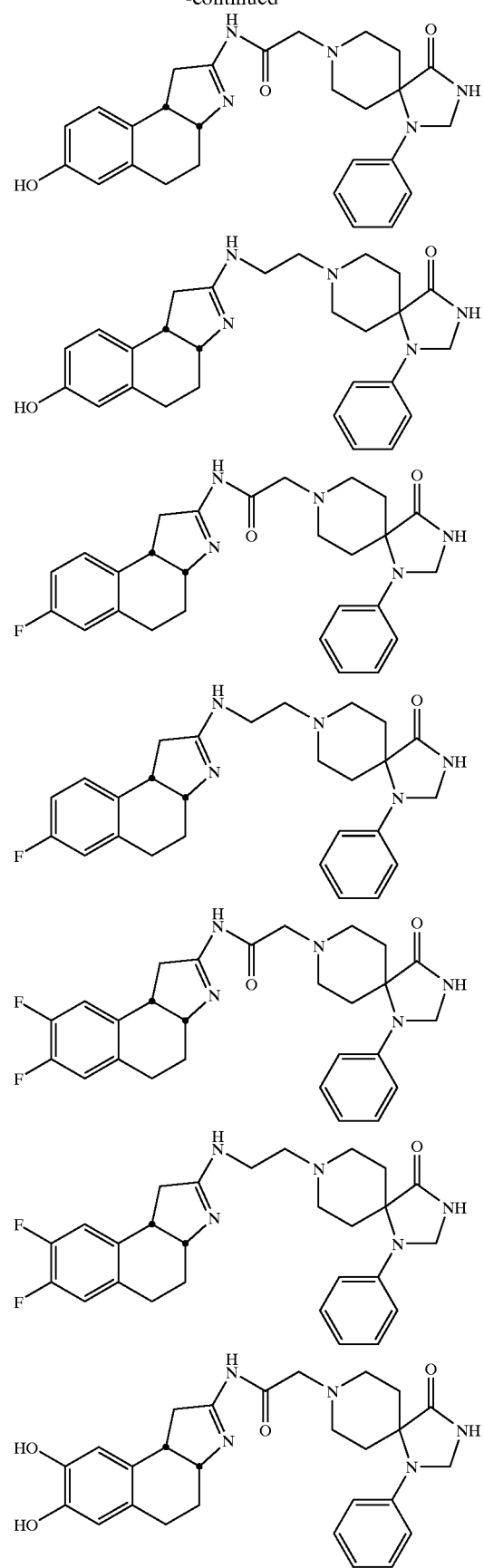
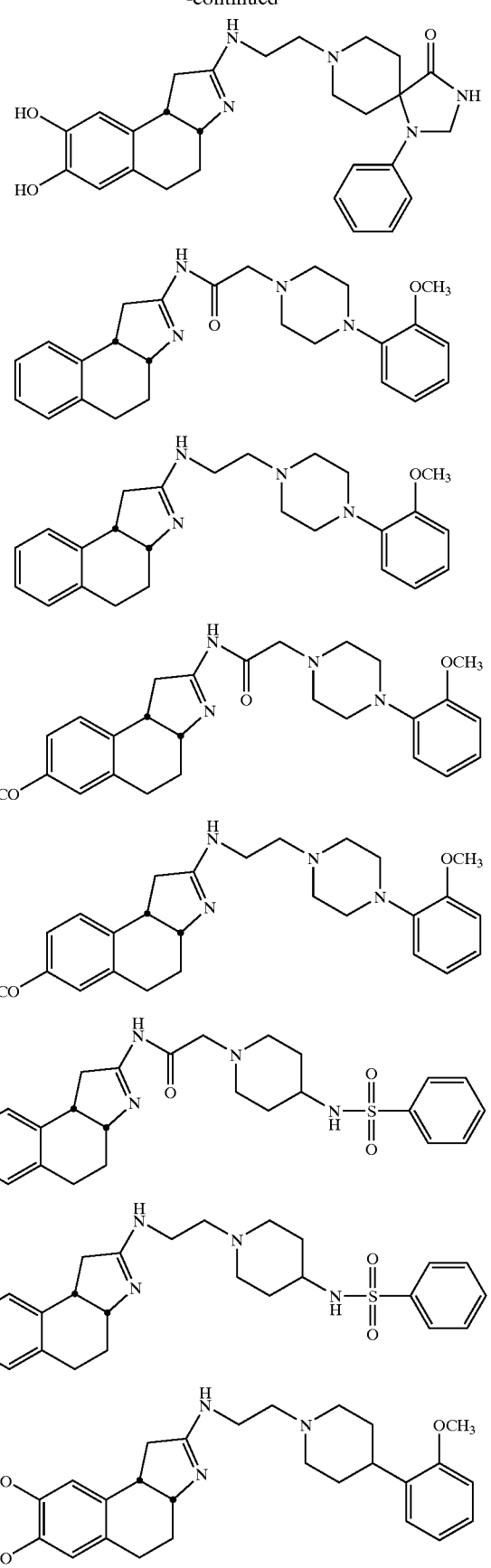

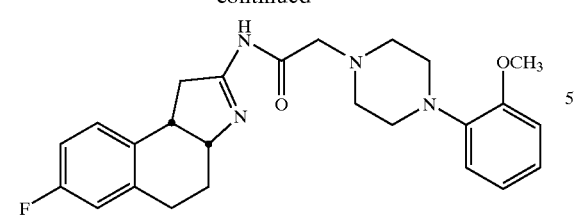
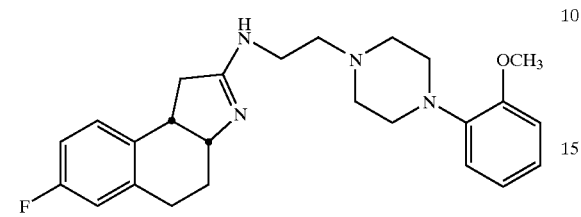
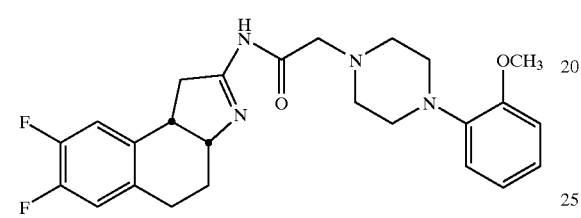
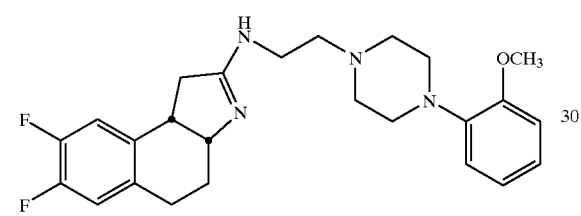
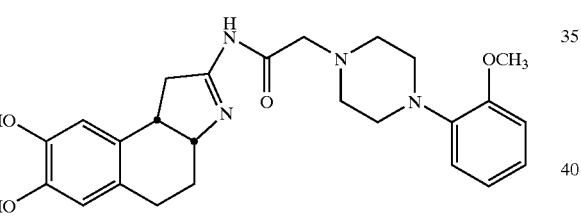
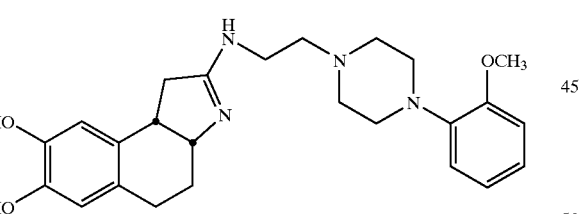
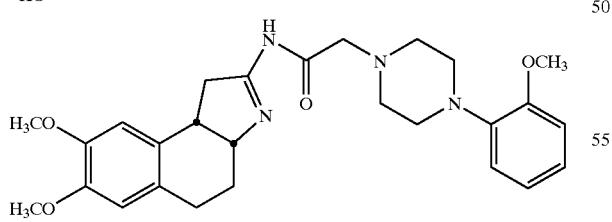
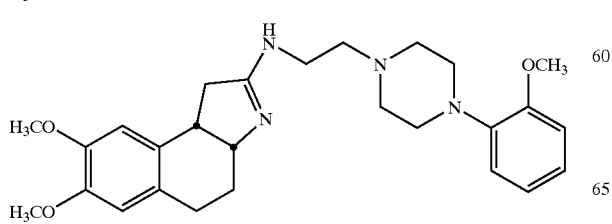
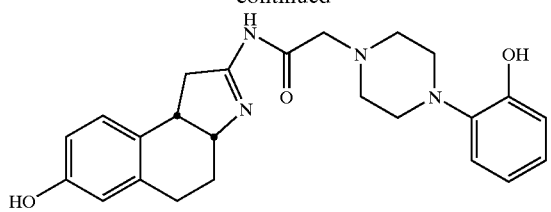
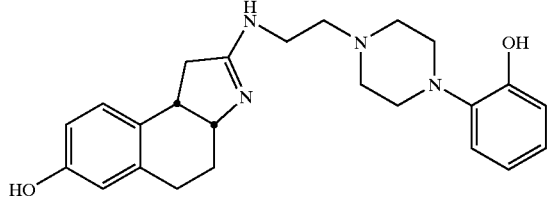
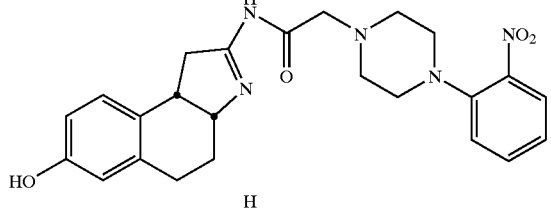
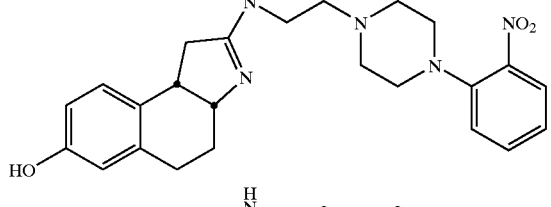
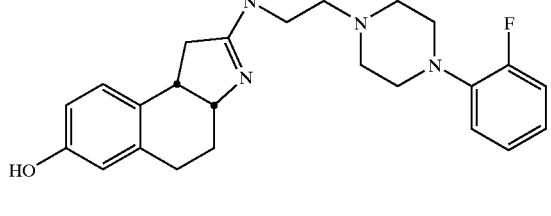

DETAILED DESCRIPTION OF THE INVENTION

The cyclic amidines of formula A that comprise this invention are synthesized via several distinct chemical syntheses which are described in detail in the Examples set forth below. In general, each synthetic route consists of several sequential chemical operations which are outlined in Schemes 1–8 and which can be generalized as described below:

Introduction of the α-cyanomethyl group onto a β-tetralone nucleus.

Concomitant reductive amination/cyclization to produce amidine intermediates.

Acylation of cyclic amidine intermediates to afford compounds of formula A in which Y=carbonyl (C=O).

Reduction of the amide to generate the cyclic amidines of formula A in which Y=methylene (—CH$_2$—).

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org.*

*Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halohydrocarbon solvents. In those cases wherein the product is isolated as the acid addition salt, the free base is obtained by techniques known to those skilled in the art.

Specifically, an appropriately substituted β-tetralone (I) is reacted with a secondary amine such as pyrrolidine in an inert halohydrocarbon solvent such as, for example, dichloromethane or a hydrocarbon solvent such as benzene for example, under Dean-Stark conditions (removal of water) or in an ethereal solvent such as tetrahydrofuran or an alcohol solvent such as methanol, at a temperature ranging from ambient temperature to reflux, to afford enamine (II). Cyanomethylation of enamine (II) is accomplished by reaction with an α-haloacetonitrile, such as bromoacetonitrile, in an inert solvent such as acetonitrile, at a temperature ranging from ambient temperature to reflux, to afford the iminium salt (III). The iminium salt is hydrolyzed by treatment with an aqueous acid solution, such as hydrochloric or acetic acid, which may contain an organic solvent such as an alcohol or dioxane to facilitate dissolution and reaction, to afford the α-cyanomethyl-β-tetralone (IV). Reductive amination and concomitant cyclization of tetralone (IV) is accomplished by reaction with a reducing agent such as, for example, sodium cyanoborohydride, and an ammonium equivalent such as, for example, ammonium acetate, in an alcohol solvent such as methanol or in a halohydrocarbon solvent such as dichloromethane, at a temperature ranging from ambient temperature to reflux. An organic acid, such as acetic acid for example, may be added to facilitate this transformation; cyclization under these reaction conditions typically affords the cis-amidine (V) as the major product. Amidine (V) may be converted to its acid addition salt upon treatment with organic acids such as trifluoroacetic acid, or via treatment with inorganic acids such as hydrochloric acid, to afford the corresponding amidine salt (VI) (Scheme 1). HX in Scheme 1 represents the hydrochloride salt.

Scheme 1

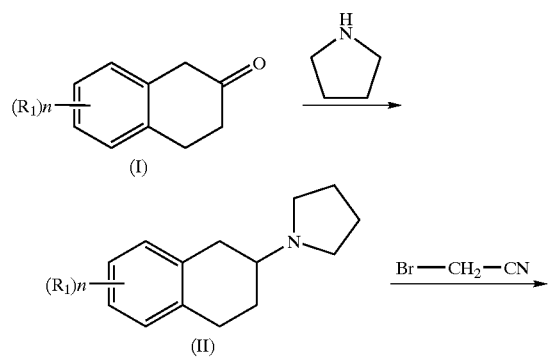

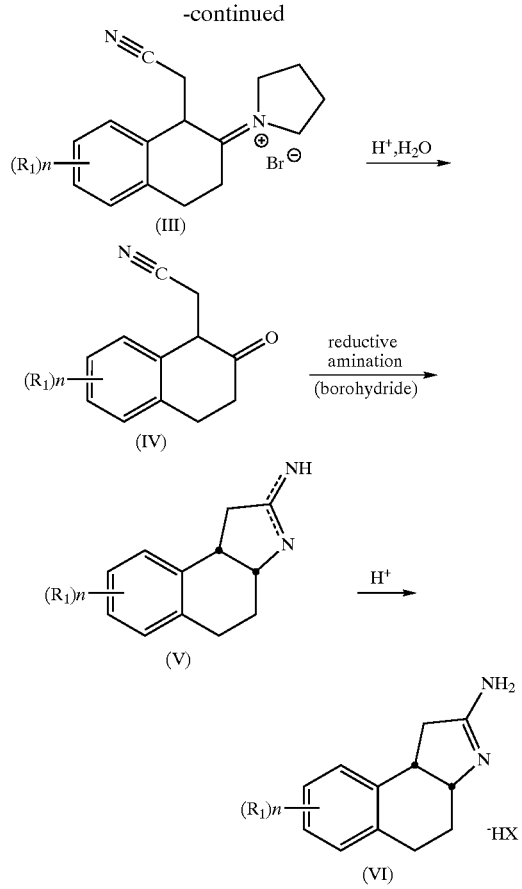

The amidine products described above ((V) and (VI)) are acylated via suitable amidation methods (see Gross and Meienhofer, Eds., "*The Peptides*", Vols. 1–3, Academic Press, New York, N.Y., 1979–1981). A carboxylic acid is converted to an activated ester via peptide coupling methods known to those skilled in the art, and the product of this reaction is subsequently reacted with amidine (V) or (VI) to afford the corresponding amide product. For example, trans-4-(benzenesulfonamido)methylcyclohexane carboxylic acid is reacted with HBTU (2-(1H-benzotriazole-1-yl)-1,1,3,3-tetramethyluronium hexafluorophosphate and amidine (VI) in the presence of a base such as diisopropylethylamine, in an inert solvent such as N,N-dimethylformamide, at a temperature from ambient temperature to reflux, to afford sulfonamides (VII) of formula A in which Y=carbonyl and Z=(aryl)sulfonamido (Scheme 2). Reaction of amidine (VI) or (V) with alkyl- or heteroaryl-sulfonyl halides, under similar conditions, affords sulfonamides (VIII) of formula A. During these transformations, minor amounts of regiomers (IX) and (X) are formed respectively; compounds of this type are considered to be part of this invention as well.

Scheme 2

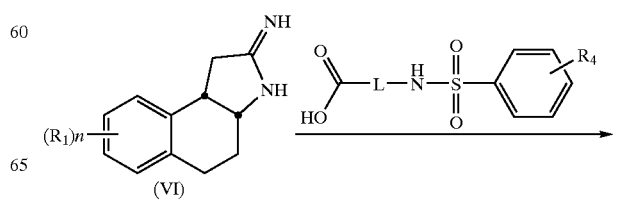

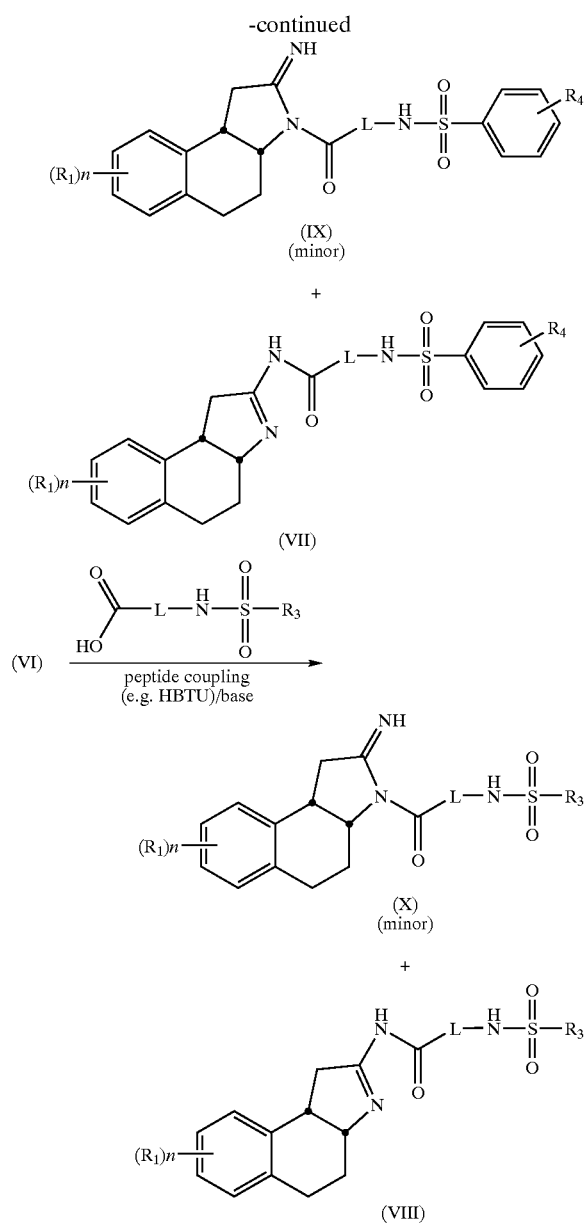

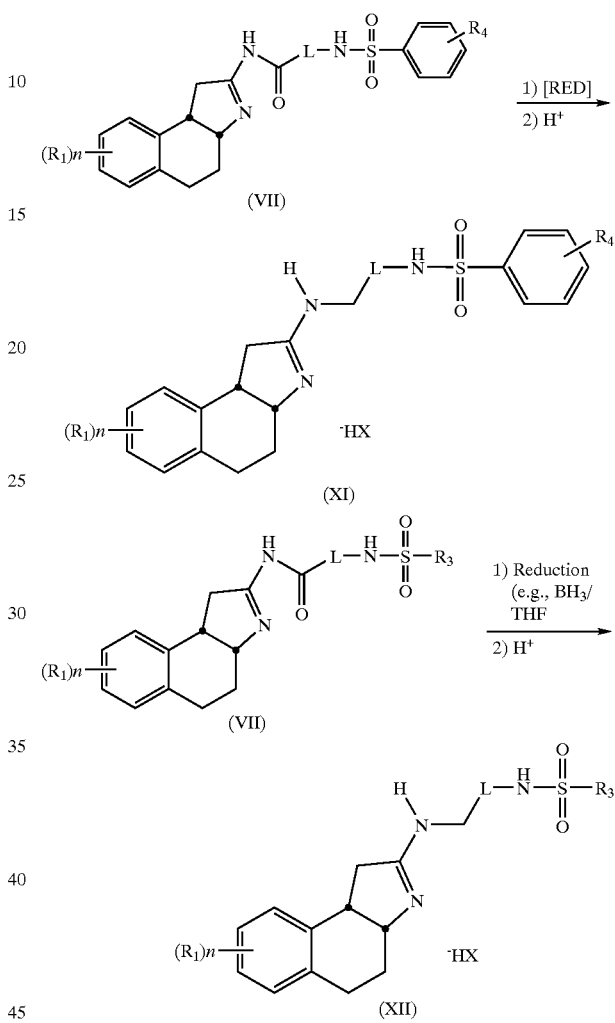

sponding free bases. Preferably, these materials are isolated as an acid addition salts upon treatment with a suitable organic acid such as trifluoroacetic acid or inorganic acid such as hydrochloric acid (Scheme 3).

Alternatively, a sulfonamido-carboxylic acid is first treated with an amine base, such as triethylamine, in an inert hydrocarbon, ethereal or halohydrocarbon solvent, such as dichloroethane, and subsequently reacted with isobutyl chloroformate at a temperature from about −20° C. to 80° C. This resulting mixture is then reacted with amidine (V), in a suitable inert solvent such dichloromethane at a temperature from about −20° C. to reflux, to afford the sulfonamides (VII) and (VIII) of formula A respectively, in which Y=carbonyl and Z=(aryl)sulfonamido or sulfonamido.

The amidino sulfonamides of formula A in which Y=methylene are prepared via reduction of amidino amides (VII) and (VIII) by reaction with a suitable reducing agent such as borane-tetrahydrofuran complex or lithium aluminum hydride in an inert hydrocarbon solvent such as toluene or ethereal solvent such as tetrahydrofuran, at a temperature from ambient temperature to reflux. The crude product is treated with an aqueous acid solution such as hydrochloric acid (3M–6M) in order to cleave any boron complexes; neutralization affords sulfonamides (XI) and (XII) as corresponding free bases. Reduction of the regiomeric amides (IX) and (X) by the methods described above in Scheme 3, affords amines (XIII) and (XIV) (Scheme 4).

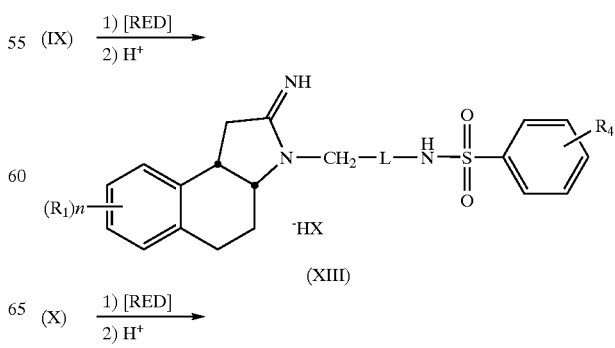

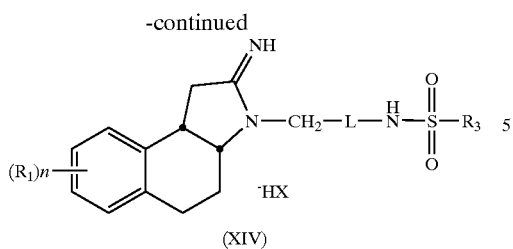

(XIV)

Compounds of formula A in which Z=2,3-dihydro-2-oxo-1H-benzimidazol-1-yl and L=(N-methylene)piperidin-4-yl are prepared from amidines (V) or (VI) and [4-(2-keto-1-benzimidazolinyl)piperidin-1-yl]acetic acid. For example, 4-(2-keto-1-benzimidazolinyl)piperidine is reacted with a bromoacetic acid ester, such as ethyl bromoacetate, in the presence of an amine base, such as diisopropylethylamine, in an inert solvent such as acetonitrile, at a temperature ranging from ambient temperature to reflux, to afford ethyl [4-(2-keto-1-benzimidazolinyl)piperidin-1-yl]acetate. This ester is subjected to hydrolysis under basic conditions, for example, by treatment with sodium hydroxide in an alcoholic solution such as aqueous methanol, to yield, upon acidification with an inorganic or organic acid such as hydrochloric or acetic acid for example, [4-(2-keto-1-benzimidazolinyl)piperidin-1-yl]acetic acid. This carboxylic acid is reacted directly with amidine (V) or (VI), in the presence of an amine base, under peptide coupling conditions described above, to afford amidino benzimidazolinones (XV) of formula A in which Y=carbonyl and L=(N-methylene)piperidin-4-yl (Scheme 5).

Scheme 5

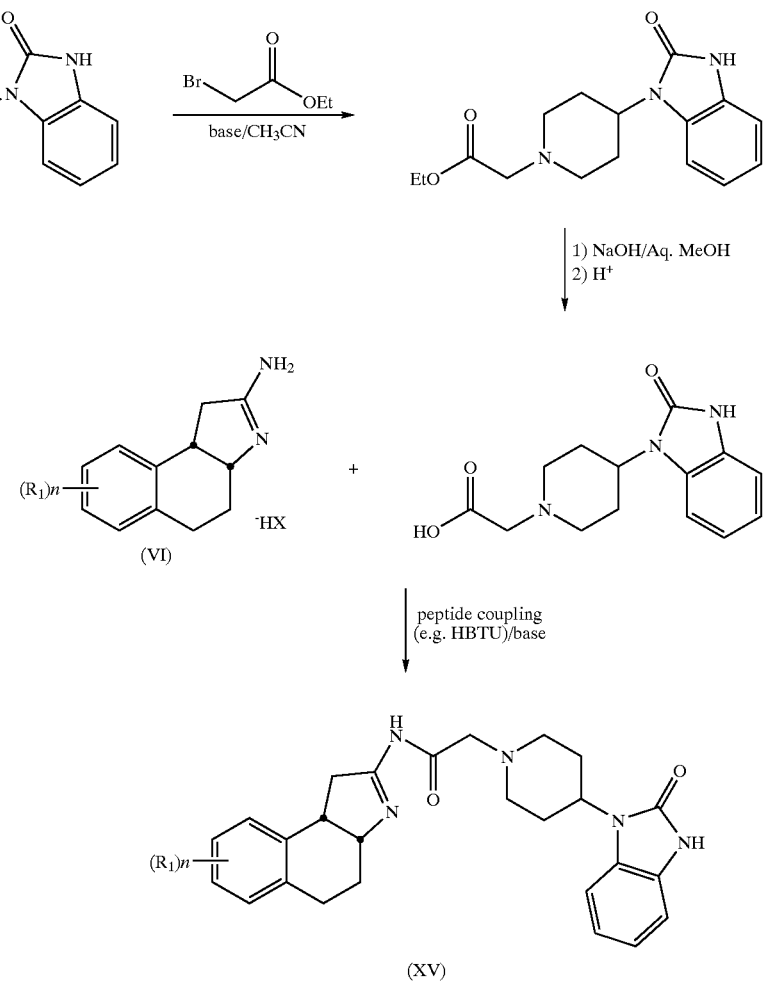

Compounds (XVI) of formula A in which Y=methylene and L=(N-methylene)piperidin-4-yl and Z=2,3-dihydro-2-oxo-1H-benzimidazol-1-yl are prepared by reduction of amides (XV) with a reducing agent such as borane-tetrahydrofuran complex or lithium aluminum hydride as described above (Scheme 6).

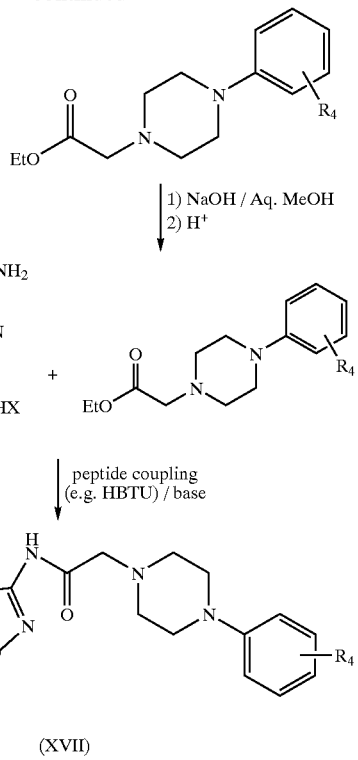

Compounds of formula A in which Y=carbonyl, L=(N-methylene)piperazin-4-yl and Z=phenyl are prepared by reacting a phenylpiperazine with a haloacetic acid ester, such as, for example, ethyl bromoacetate, in the presence of an amine base, such as diisopropylethylamine, in an inert solvent such as acetonitrile, at a temperature ranging from ambient temperature to reflux, to afford ethyl (4-arylpiperazin-1-yl)acetate. This ester is subjected to hydrolysis under basic conditions, for example, by treatment with sodium hydroxide in an aqueous methanol, to yield, upon acidification with an inorganic or organic acid such as hydrochloric or acetic acid for example, (4-arylpiperazin-1-yl)acetic acid. This carboxylic acid is reacted directly with amidine (V) or (VI) in the presence of a base, such as triethylamine for example, under peptide coupling conditions described above, to afford arylpiperidines (XVII) of formula A in which Y=carbonyl, L=(N-methylene)piperazin-4-yl and Z=aryl or substituted aryl (Scheme 7).

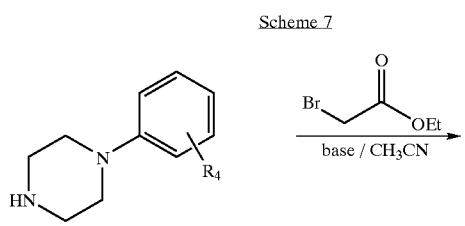

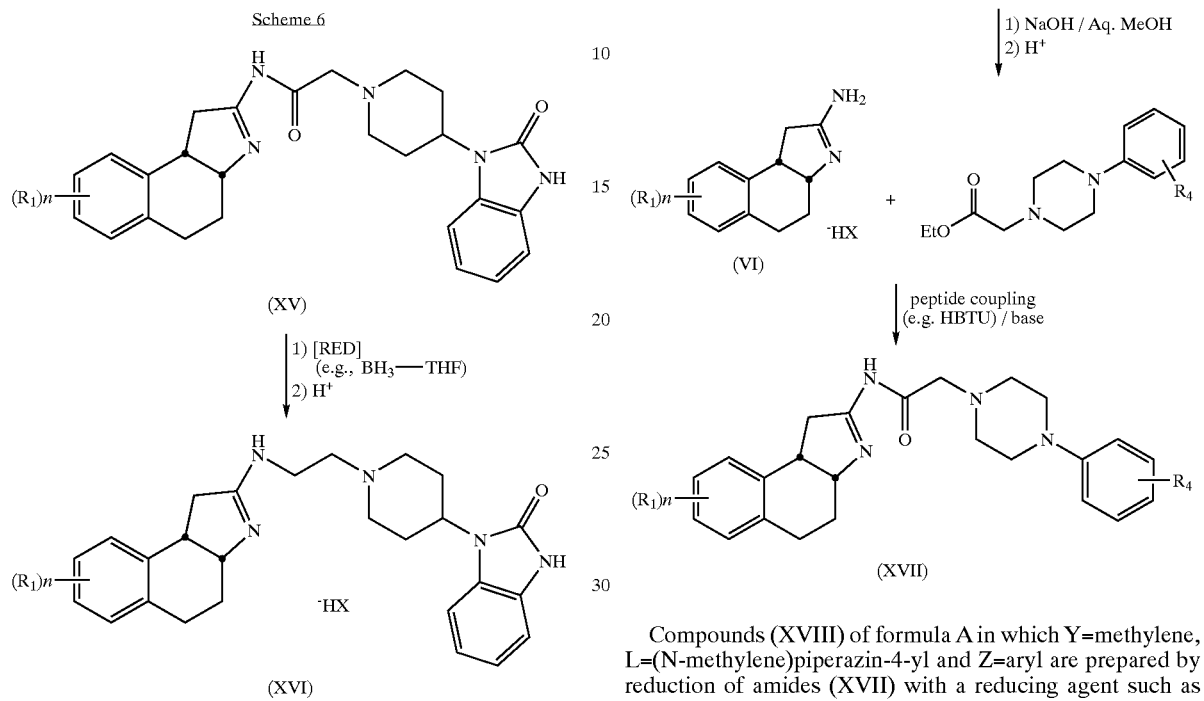

Compounds (XVIII) of formula A in which Y=methylene, L=(N-methylene)piperazin-4-yl and Z=aryl are prepared by reduction of amides (XVII) with a reducing agent such as borane-tetrahydrofuran complex or lithium aluminum hydride (Scheme 8). Replacement of (4-arylpiperazin-1-yl) acetic acid with a (4-arylpiperidin-1-yl)acetic acid in Schemes 7 and 8 affords compounds of formula A in which L=(N-methylene)piperidin-4-yl and Z=aryl.

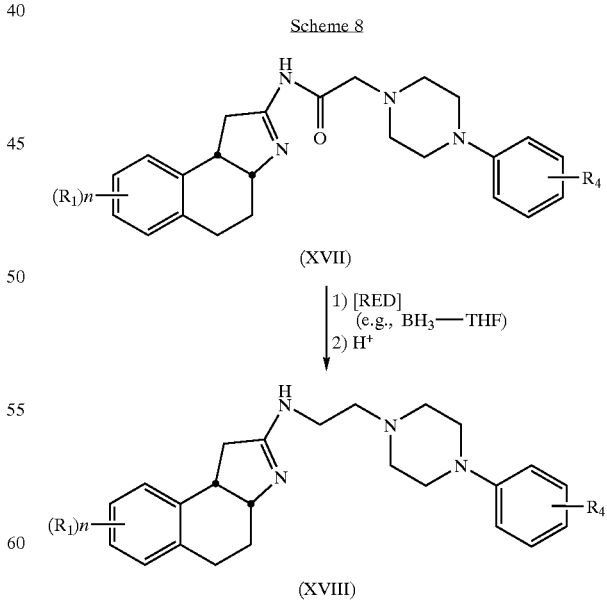

Compounds of formula A in which Y=carbonyl, L=(N-methylene)piperidin-4,4-diyl and Z=1-aryl-2,3-dihydro-4-oxo-imidazol-5,5-diyl are prepared by reacting 1-aryl-1,3,8-triazaspiro-[4,5]decan-4-one with a haloacetic acid ester, such as ethyl bromoacetate, in the presence of an amine base, such as diisopropylethylamine, in an inert solvent such as acetonitrile, at a temperature from ambient temperature to reflux, to afford ethyl (1-aryl-1,3,8-triazaspiro-[4,5]decan-4-one-8-yl)acetate. This ester is subjected to hydrolysis under basic conditions, for example, by treatment with sodium hydroxide in an alcoholic solution such as aqueous methanol, to yield upon acidification with an inorganic or organic acid such as hydrochloric or acetic acid for example, (1-aryl-1,3,8-triazaspiro-[4,5]decan-4-one-8-yl)acetic acid. This carboxylic acid is reacted directly with amidine (V) or (V), in the presence of a base such as triethylamine for example, under peptide coupling conditions described above, to afford amides (XIX) of formula A in which Y=carbonyl, L=(N-methylene)piperidin-4,4-diyl and Z=1-aryl-2,3-dihydro-4-oxo-imidazol-5,5-diyl (Scheme 9).

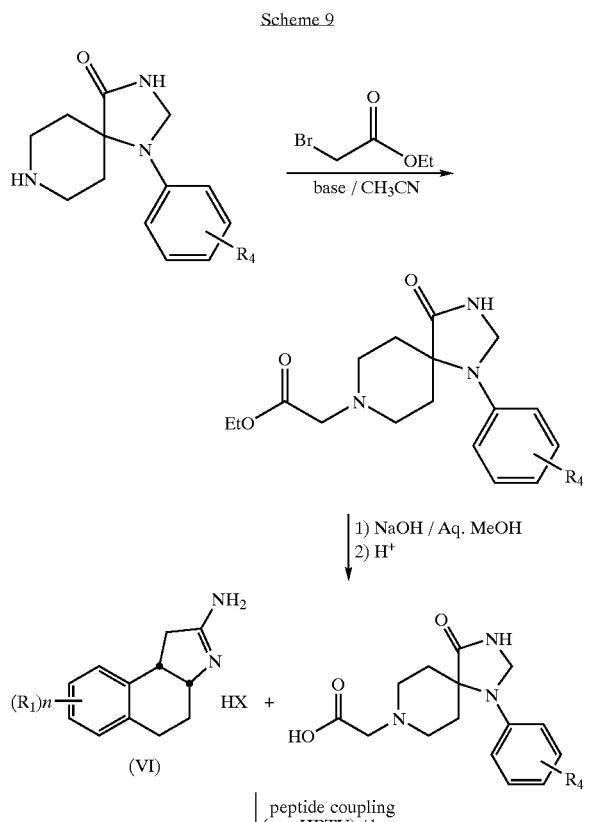

Other compounds of this invention having the formula A can be prepared using the methods described herein; modifications of the experimental protocols described above are known or obvious or within the ability of those skilled in the art. For example, a variety of β-tetralones are known or readily prepared by reaction of phenylacetic acids with ethylene gas in the presence of a Lewis acid (for example, Stjernlof, P. et. al. *J. Med. Chem.* 1995, 38, 2202). Compounds in which the $R_1$ group(s) is varied are obtained using this chemistry; in some cases, protecting group manipulations are used and these are obvious or known to those skilled in the art. Examples include masking an amine group as a carbamate, amide or phthalamide, and masking an hydroxyl group as an ether or ester. Other $R_1$ substituents are available through (other) functional group manipulations such as, for example, reduction of a nitro group to an amine or dehydration of an amide to a nitrile.

Compounds in which the L group is varied, are derived from amino-carboxylic acids or piperazines or piperidines; hundreds of such compounds are commercially available and many more are known. Compounds of formula A where Z=sulfonamido or (aryl)sulfonamido, in which either the $R_3$ or the $R_4$ group is varied, are accessible by sulfonylation; there are hundreds of sulfonyl halides or sulfonic acids that are commercially available and more that are known. Compounds of formula A where Z=sulfonamido or (aryl) sulfonamido, in which the $R_3$ substituent is heteroaryl can be prepared by substituting a pyridinyl, thienyl or furyl sulfonylchloride for a benzenesulfonamide as described in Scheme 2. N-alkylimidazolylsulfonyl chlorides can be used to prepare sulfonamides of formula A in which the $R_3$ substituent is imidazolyl. Similarly, alkylsulfonyl and cycloalkylsulfonyl halides, alone or in the presence of an activating agent such as a Lewis acid, can be used to prepare sulfonamides of formula A in which the $R_3$ substituent is alkyl or cycloalkyl respectively.

Compounds of formula A with L groups other than methylene are prepared by substituting bromoacetic acid esters with other Ω-bromo acid esters in Schemes 5, 7 and 9. There are hundreds of Ω-bromo acids and esters that are either commercially available or known. Compounds of formula A in which the L group is alkylene are derived from arylalkylenecarboxylic acids; many compounds of this structural type are either commercially available or known. Similarly, arylalkenylene-, arylalkynylene- and arylcycloalkylene-carboxylic acids are known or available and can be used to make compounds of formula A in which L is alkenylene, alkynylene or cycloalkylene respectively.

Compounds in which $B_2$ is other than hydrogen are made starting from an appropriate α-methylated-β-tetralone and carrying out the chemistry described in Scheme 1 and subsequent schemes and examples. Compounds in which $R_2$ is other than hydrogen are made by reaction of a cyclic amidine with an alkylation agent such as methyl iodide.

EXAMPLES

The following examples describe the invention in greater detail and are intended to illustrate the invention, but not to limit it. All compounds were identified by a variety of methods including nuclear magnetic resonance spectroscopy, mass spectrometry and in some cases, infrared spectroscopy and elemental analysis. Nuclear magnetic resonance (300 MHz NMR) data are reported in parts per million downfield from tetramethylsilane. Mass spectra data are reported in mass/charge (m/z) units. Unless otherwise noted, the materials used in the examples were obtained from readily available commercial sources or synthesized by standard methods known to those skilled in the art.

Example 1 trans-4-[[(Phenylsulfonyl)amino]methyl]-N-(cis-3a, 4,5,9b-tetrahydro-7-methoxy-1H-benz[e]indol-2-yl) cyclohexanecarboxamide (7)

1-(3,4-Dihydro-6-methoxynaphthalen-2-yl)-pyrrolidine (2)

A solution of 6-methoxy-3,4-dihydro-1H-naphthalen-2-one (1) (5.64 g, 32 mmol) in methanol (60 mL) was treated with pyrrolidine (3.5 mL, 41.6 mmol) and the resultant mixture was stirred at ambient temperature for 1.5 h. The product precipitated from solution within minutes of the addition of pyrrolidine. The resultant suspension was cooled in an ice bath and the enamine product (2) was collected by filtration as a white solid (5.6 g, 76%). NMR (CDCl$_3$): δ 1.86–1.94 (m, 4 H), 2.46 (t, 2H), 2.80 (t, 2 H), 3.19–3.25 (m, 4 H), 3.77 (s, 3 H), 5.10 (s, 1 H), 6.59–6.65 (m, 2 H) and 6.78 d, 1 H).

1-[1-(Cyanomethyl)-3,4-dihydro-6-methoxy-2(1H)-naphthalenylidene)]pyrrolidinium bromide (3)

A solution of 1-(3,4-dihydro-6-methoxynaphthalen-2-yl)-pyrrolidine (2) (5.6 g, 24.4 mmol) in acetonitrile (60 mL) was treated with bromoacetonitrile (2.21 mL, 31.7 mmol). The resultant solution was stirred at ambient temperature for 1 h. The pyrrolidinium salt (3), was collected by filtration and washed with diethyl ether, to give the pyrrolidinium bromide as a hygroscopic colorless solid which was used directly in the subsequent reaction. MS 269 (M$^+$).

(1,2,3,4-Tetrahydro-6-methoxy-2-oxo-naphthalen-1-yl)-acetonitrile (4)

A solution of 1-[1-(cyanomethyl)-3,4-dihydro-6-methoxy-2(1H)-naphthalenylidene)]pyrrolidinium bromide (3) (24.4 mmol) and acetic acid (5 mL) in dichloromethane/methanol/water (60 mL/100 mL/50 mL) was stirred at ambient temperature for 18 h. An organic layer was separated and the aqueous layer was extracted with dichloromethane (100 mL). The combined organics were washed with water, then washed with a saturated solution of aqueous sodium bicarbonate, and dried over magnesium sulfate. The solvent was evaporated in vacuo to give the α-cyano-β-tetralone product (4) as a brown oil (3.3 g, 63%, 2 steps). IR(neat): 1715, 1722, 2251 cm$^{-1}$; NMR(CDCl$_3$): δ 2.47–2.58 (m, 1 H), 2.67–2.80 (m, 1 H), 2.88–3.13 (m, 4 H), 3.77 (t, 1 H), 3.77 (s, 3 H), 6.81–6.90 (m, 2 H), 7.19 (d, 1 H).

3a,4,5,9b-Tetrahydro-7-methoxy-1H-benzo[e]indol-2-yl)-amine (5) and 3a,4,5,9b-tetrahydro-7-methoxy-1H-benzo[e]indol-2-yl)amine hydrochloride (6)

A solution of (1,2,3,4-tetrahydro-6-methoxy-2-oxo-naphthalen-1-yl)-acetonitrile (4) (3.5 g, 16.2 mmol) and ammonium acetate (18.8 g, 0.24 mol) in methanol (50 mL) was stirred at ambient temperature for 15 min. Sodium cyanoborohydride (5.11 g, 0.081 mol) was added and the resultant solution was heated at reflux for 1 h. The solvent was evaporated in vacuo, and the residue was treated with a solution of sodium hydroxide (12 g, 0.3 mol) in water (100 mL) at 0° C. A pale gray solid precipitated out of solution and was collected by filtration, washed with water and triturated in diethyl ether to give the crude cyclic amidine (5) (3.5 g, 100%). This material (3.0 g, 13.8 mmol) was dissolved in tetrahydrofuran/methanol (~9:1, 75 mL) and treated with 1 M hydrochloric acid in diethyl ether (40 mL) at 0° C. to induce precipitation. The resultant precipitate was collected by filtration and washed with diethyl ether to give 3a,4,5,9b-tetrahydro-7-methoxy-1H-benzo[e]indol-2-yl)-amine hydrochloride (6) (1.57 g, 45%) as an off white solid. IR(KBr): 1611, 1681, 1703, 2832, 3106 cm$^{-1}$; NMR (DMSO-d$_6$): δ 1.79–1.91 (m, 2 H), 2.60–2.74 (m, 3 H), 3.33–3.46 (m, 1 H), 3.63–3.73 (m, 1 H), 3.71 (s, 3 H), 6.80 (d, 1 H), 6.71 (d of d, 1 H), 7.17 (d, 1 H), 9.08 (br s, 1 H), 9.34 (br s, 1 H) and 10.06 (br s, 1 H); MS 217 (M+H)$^+$. (FIG. 1).

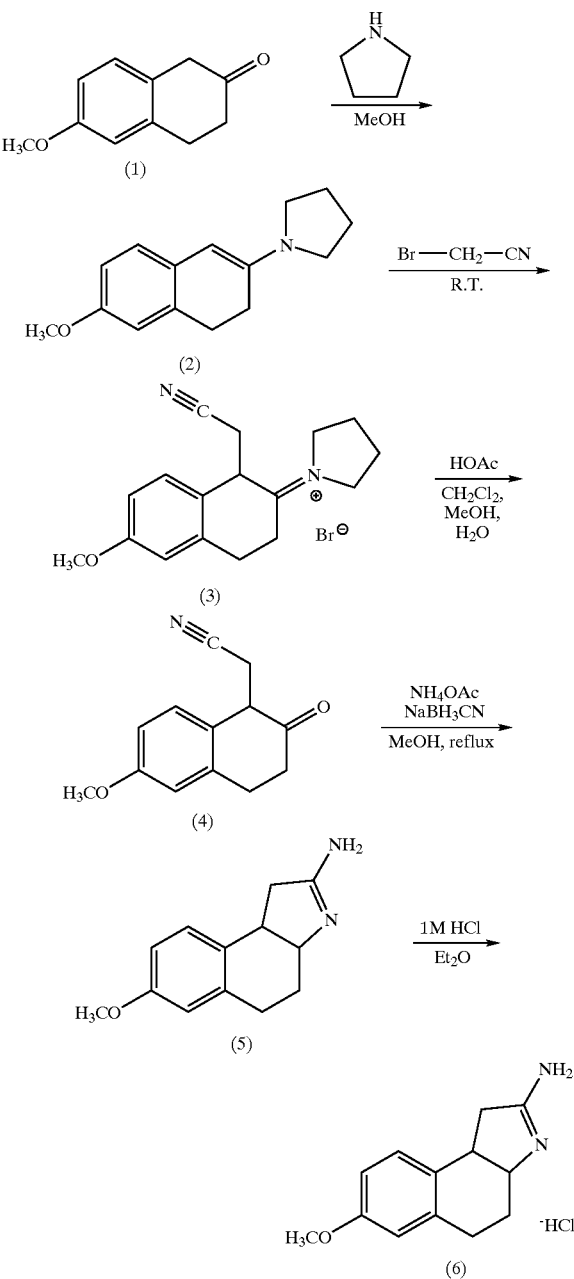

FIG. 1 trans-4-[[(Phenylsulfonyl)amino]methyl]-N-(cis-3a,4,5,9b-tetrahydro-7-methoxy-1H-benz[e]indol-2-yl) cyclohexanecarboxamide (7)

A solution of trans-4-(benzenesulfonamido) methylcyclohexane carboxylic acid (1.16 g, 4.15 mmol), O-benzotriazol-1-yl-N,N,N',N'-tetramethyluronium hexafluorophosphate (1.58 g, 4.15 mmol) and N,N-diisopropylethylamine (2.41 mL, 13.8 mmol) in N,N-dimethylformamide (15 mL) was stirred at ambient temperature for 15 min. After this time, 3a,4,5,9b-tetrahydro-7-methoxy-1H-benzo[e]indol-2-yl)-amine hydrochloride (6) (1.0 g, 3.96 mmol) was added, and the resultant solution was heated to 45° C. for 1.5 h. The solution was then poured into ice water and the product which precipitated was collected by filtration, washed with water and air dried. This solid was triturated in diethyl ether to give trans-4-[[(phenylsulfonyl)amino]methyl]-N-(cis-3a,4,5,9b-tetrahydro-7-methoxy-1H-benz[e]indol-2-yl)cyclohexanecarboxamide (7) as a colorless solid (1.87 g, 95%). NMR (DMSO-d$_6$): δ 0.69–0.89 (m, 2 H), 1.10–1.34 (m, 3 H), 1.63–1.88 (m, 5 H), 2.10–2.27 (m, 1 H), 3.24–3.50 (m, 3 H), 3.70 (s, 3 H), 4.04–4.13 (m, 1 H), 6.63 (d, 1 H), 6.74 (d of d, 1 H), 7.05 (d, 1 H), 7.54–7.67 (m, 4 H) and 7.74–7.83 (m, 2 H); MS 496 (M+H)$^+$. (FIG. 2).

Example 2

N-[[trans-4-[[(cis-3a,4,5,9b-tetrahydro-7-methoxy-1H-benz[e]indol-2-yl)amino]methyl]cyclohexyl]methyl]benzenesulfonamide (8)

trans-4-[[[(Phenylsulfonyl)amino]methyl]-N-(cis-3a,4,5,9b-tetrahydro-7-methoxy-1H-benz[e]indol-2-yl]cyclohexanecarboxamide (7) (1.6 g, 3.22 mmol) was added in portions, with stirring, to a solution of lithium aluminum hydride (16.1 mmol) in tetrahydrofuran (36 mL) at ambient temperature. The resultant solution was heated at reflux for 45 min. The solution was then cooled on an ice bath, and then a solution of water (0.65 mL) in tetrahydrofuran (5 mL) was carefully added, followed by the addition of ten percent aqueous sodium hydroxide (0.65 mL) and water (2.1 mL). The resultant suspension, which formed, was stirred at ambient temperature for 30 min and then dried over sodium sulfate. The insoluble inorganic material was removed by filtration, and washed generously with tetrahydrofuran. The solvent was evaporated in vacuo, the residue was dissolved in a minimum amount of isopropanol and this solution was treated with a concentrated solution of hydrogen chloride in isopropanol. The solvents were evaporated in vacuo to give crude give N-[[trans-4-[[(cis-3a,4,5,9b-tetrahydro-7-methoxy-1H-benz[e]indol-2-yl)amino]methyl]cyclohexyl]methyl]benzenesulfonamide hydrochloride salt as a pale pink solid (1.38 g; estimated purity ~75% by HPLC). A 300 mg. portion of this material was purified by preparative HPLC on a C18 reverse phase column (4 cm by 45 cm), eluted with a gradient of water/acetonitrile/trifluoroacetic acid from 90/10/0.1 to 10/90/0.1 (v/v) (flow rate of 40 mL per minute) over 50 minutes. The product obtained was converted to the hydrochloride salt with ethanolic hydrogen chloride to give pure give N-[[trans-4-[[(cis-3a ,4,5,9b-tetrahydro-7-methoxy-1H-benz[e]indol-2-yl)amino]methyl]cyclohexyl]methyl]benzenesulfonamide hydrochloride (8) as a colorless solid (0.15 g). NMR (DMSO-d$_6$): δ 0.70–0.94 (m, 4 H), 1.20–1.50 (m, 2 H), 1.62–1.77 (m, 4 H), 1.80–1.94 (m, 2 H), 2.55–2.73 (m, 5 H), 3.03–3.16 (m, 2 H), 3.31–3.46 (m, 1 H), 3.63–3.73 (m, 1 H), 3.71 (s, 3 H), 4.24–4.32 (m, 1 H), 6.70 (d, 1 H), 6.79 (d of d, 1 H), 7.14 (d, 1 H), 7.55–7.67 (m, 4 H), 7.74–7.82 (m, 2 H), 9.66 (br t, 1 H) and 10.09 (br s, 1 H); MS 482 (M+H)$^+$. (FIG. 2).

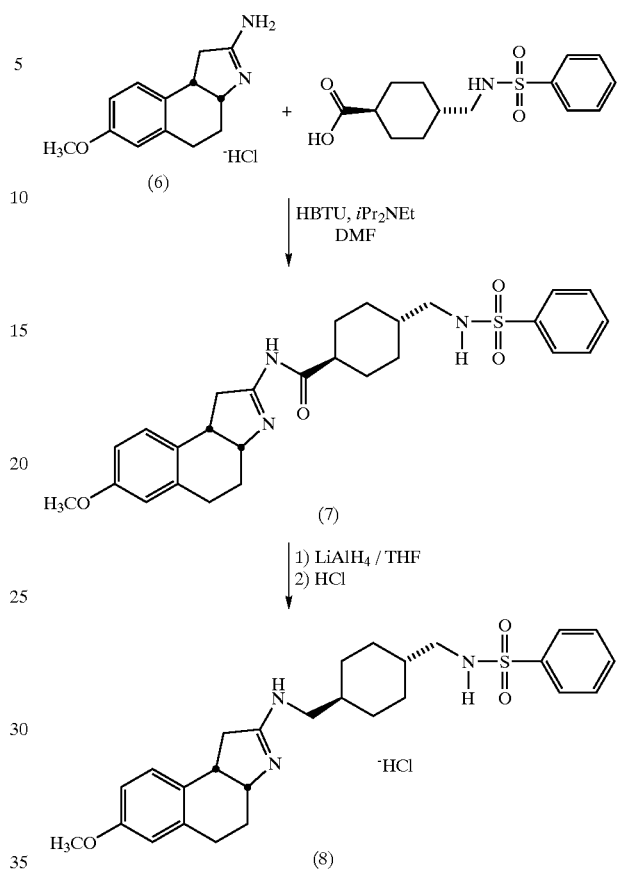

FIG. 2

Example 3 trans-4-[[(Phenylsulfonyl)amino]methyl]-N-(cis-3a,4,5,9b-tetrahydro-7-hydroxy-1H-benz[e]indol-2-yl)cyclohexanecarboxamide (9)

A suspension of trans-4-[[(phenylsulfonyl)amino]methyl]-N-(cis-3a,4,5,9b-tetrahydro-7-methoxy-1H-benz[e]indol-2-yl)cyclohexanecarboxamide (7) (0.200 g, 0.403 mmol) in dichloromethane (2 mL) was added dropwise with stirring, to a solution of boron tribromide (1.6 mmol) in dichloromethane (12 mL) at 0° C. The resultant suspension was stirred at 0° C. for 30 min. Methanol (~1 mL) was added at which point the mixture became a clear yellow solution. The solution was stirred for 30 min at 0° C. The solvents were evaporated in vacuo, and the residue was purified by preparative HPLC on C$_{18}$ reverse phase column, using water/acetonitrile/trifluoroacetic acid (50:50:0.1) as the eluent. The product obtained was dissolved in a minimum amount of methanol and converted to the hydrochloride salt by treatment with ethanolic hydrogen chloride. The solvents were evaporated in vacuo and the residue was triturated with diethyl ether to give trans-4-[[(phenylsulfonyl)amino]methyl]-N-(cis-3a,4,5,9b-tetrahydro-7-hydroxy-1H-benz[e]indol-2-yl)cyclohexanecarboxamide (9) as a beige solid (0.093 g, 45%). NMR (DMSO-d$_6$): δ 0.77–0.95 (m, 2 H), 1.20–1.37 (m, 3 H), 1.64–1.80 (m, 2 H), 1.83–1.98 (m, 3 H), 2.43–2.64 (m, 5 H), 2.91 (d of d, 1 H), 3.48–3.74 (m, 4 H), 4.37–4.47 (m, 1 H), 6.54 (d, 1 H), 6.65 (d of d, 1 H), 7.03 (d, 1 H), 7.53–7.83 (m, 6 H), 9.37 (br s, 1 H), 11.56 (br s, 1 H), 13.22 (br s, 1 H); MS 482 (M+H)+ (FIG. 3).

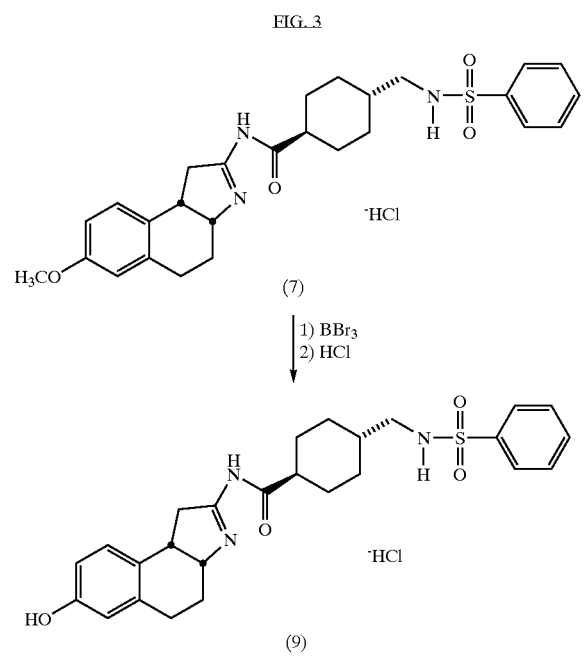

FIG. 3

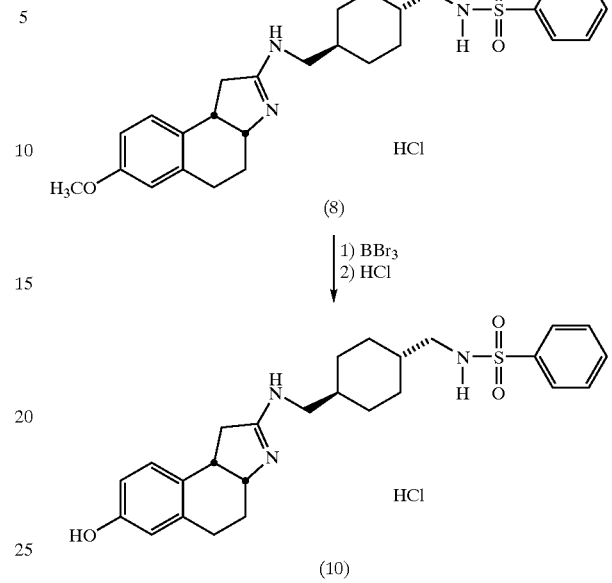

FIG. 4

Example 4

N-[[trans-4-[[(cis-3a,4,5,9b-t trahydro-7-hydroxy-1H-benz[e]indol-2-yl)amino]methyl]cyclohexyl]methyl]benzenesulfonamide hydrochloride (10)

A solution of boron tribromide (3.4 mmol) in dichloromethane (3.4 mL) was added to a solution of N-[[trans-4-[[(cis-3a,4,5,9b-tetrahydro-7-methoxy-1H-benz[e]indol-2-yl)amino]methyl]cyclohexyl]methyl]benzenesulfonamide hydrochloride (8) (0.37 g, 0.714 mmol) and triethylamine (0.235 mL, 1.69 mmol) in dichloromethane (20 mL) at 0° C. The resultant mixture was stirred at 0° C. for 1 h, and stirring was continued at room temperature for an additional 1 h. The mixture was cooled on an ice bath and methanol was added. After stirring for several minutes, the solvents were evaporated In vacuo. The residue was purified by preparative HPLC on a C18 reverse phase column, eluted with water/acetonitrile/trifluoroacetic acid (~50:50:0.1). The product was dissolved in a minimum amount of methanol and converted to the hydrochloride salt with ethanolic hydrogen chloride. The solvents were evaporated in vacuo to give N-[[trans-4-[[(cis-3a,4,5,9b-tetrahydro-7-hydroxy-1H-benz[e]indol-2-yl)amino]methyl]cyclohexyl]methyl]benzenesulfonamide hydrochloride as a colorless solid (0.15 g, 42%). NMR (DMSO-$d_6$): δ 0.67–0.98 (m, 4 H), 1.21–1.50 (m, 2 H), 1.58–1.97 (m, 6 H), 2.50–2.75 (m, 5 H), 3.03–3.23 (m, 2 H), 3.31–3.46 (m, 1 H), 3.55–3.67 (m, 1 H), 4.17–4.33 (m, 1 H), 6.53 (s, 1 H), 6.64 (d, 1 H), 6.99 (d, 1 H), 7.52–7.83 (m, 6 H), 9.34 (br s, 1 H), 9.76 (br s, 1 H) and 10.24 (br s, 1 H); MS 468 (M+H)+ (FIG. 4).

Example 5

2-[[4-(2,3-Dihydro-2-oxo-1H-benzimidazol-1-yl)-1-piperidinyl]acetyl]-3a,4,5,9b-tetrahydro-1H-benzo[e]indol-2-yl)-amine (11)

A solution of 4-(2-keto-1-benzimidazolinyl)piperidine (10.0 g, 46 mmol), ethyl bromoacetate (5.1 mL, 46 mmol) and N,N-diisopropylethylamine (8.8 mL, 50.6 mmol) in acetonitrile (200 mL) was heated at reflux for 1 hour. The solvent was evaporated in vacuo, and the residue was suspended in water (~200 mL). The suspension was made basic with the addition of a saturated aqueous solution of sodium bicarbonate. The resultant solid was collected by filtration, washed with water and dried in vacuo to give the ethyl (4-(2-keto-1-benzimidazolinyl)piperidin-1-yl)acetate as a colorless solid (13.2 g, 94%). MS m/z 304 (MH+); NMR(CDCl$_3$): δ 1.32 (t, 3 H), 1.84 (br d, 2 H), 2.40–2.66 (m, 4 H), 3.13 (br d, 2 H), 3.31 (s, 2 H), 4.23 (q, 2 H), 4.45–4.49 (m, 1 H), 6.99–7.10 (m, 2 H), 7.12–7.19 (m, 1 H), 7.27–7.34 (m, 1 H) and 10.54 (brs, 1 H).

A solution of ethyl (4-(2-keto-1-benzimidazolinyl)piperidin-1-yl)acetate (13.0 g, 42.8 mmol) in methanol (150 mL) was treated with an aqueous solution of sodium hydroxide (3 N, 30 mL, 90 mmol) and heated at reflux for 2 hours. The solution was cooled to room temperature and neutralized with the addition of concentrated hydrochloric acid (12 N, 7.5 mL). The solvent was evaporated in vacuo, and the resultant amorphous solid was dried in vacuo with heating (~50° C.) overnight to give (4-(2-keto-1-benzimidazolinyl)piperidin-1-yl)acetic acid (17.2 g) which was used in the subsequent step without purification. MS m/z 304 (MH+); NMR(DMSO-$d_6$): δ 1.74 (br d, 2 H), 2.53–2.67 (m, 2 H), 2.74–2.86 (m, 2 H), 3.33 (s, 2 H), 4.29–4.42 (m, 1 H), 6.97–7.05 (m, 3 H) and 7.38–7.43 (m, 1 H).

A mixture of (4-(2-keto-1-benzimidazolinyl)piperidin-1-yl)acetic acid (2.34 g, ~5.83 mmol), 2-(1H-benzotriazole-1-yl)-1,1,3,3-tetramethyuronium hexafluorophosphate (1.87 g, 4.93 mmol) and N,N-diisopropylethylamine (3.1 mL, 17.9 mmol) in N,N-dimethylformamide (15 mL) was stirred at 45° C. for 10 min. After this time, 3a,4,5,9b-tetrahydro-1H-benzo[e]indol-2-yl)amine (1.0 g, 4.49 mmol) was added to the mixture, and the resultant solution was stirred at room temperature for an additional two hours. A white precipitate was collected by filtration and washed with water. The product was purified by flash chromatography on silica gel using 5 to 10% methanol in dichloromethane as the eluent. The product was triturated with diethyl ether and dried in vacuo to give 2-[[4-(2,3-dihydro-2-oxo-1H-benzimidazol-1-yl]-piperidinyl]acetyl]-3a,4,5,9b-tetrahydro-1H-benzo[e]indol-2-yl)-amine (11) as a colorless solid, (0.23 g, 9%). An additional 0.6 g of product was recovered from the mother liquor as well as several impure fractions of the chromatography. MS m/z 444 (MH+); NMR(CDCl$_3$): δ 1.78~2.10 (m, 4 H), 2.34–2.83 (m, 6 H), 3.00–3.17 (m, 3 H), 3.20 (s, 2 H), 3.56–3.78 (m, 2 H), 4.27–4.45 (m, 2 H) and 7.00–7.23 (m, 8 H), (FIG. 5).

FIG. 5

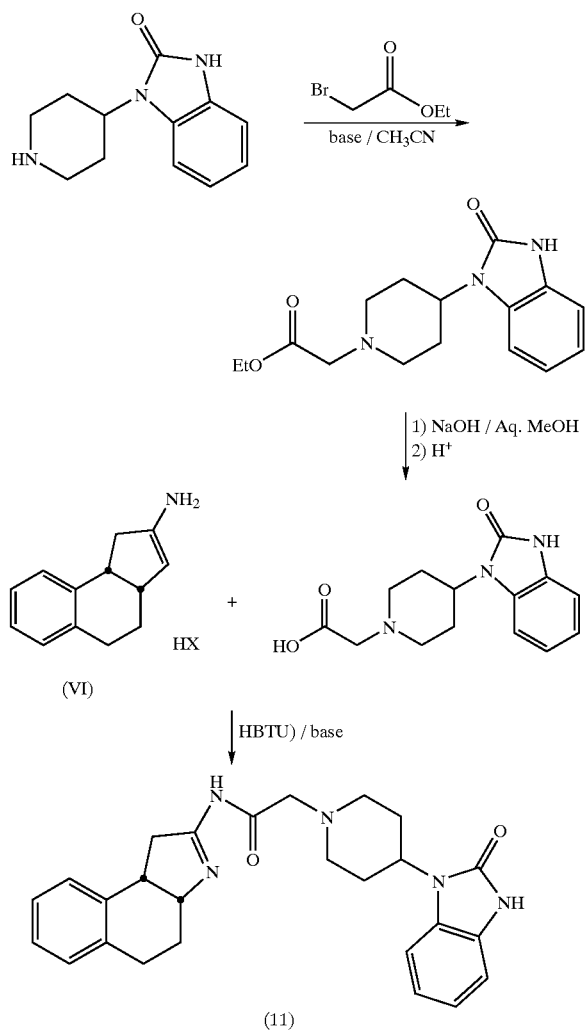

(VI)

(11)

Example 6

2-[[4-(2,3-Dihydro-2-oxo-1H-benzimidazol-1-yl)-1-piperidinyl]ethyl]-3a,4,5,9b-tetrahydro-7-methoxy-1H-benzo[e]indol-2-yl)-amine (12)

2-[[4-(2,3-Dihydro-2-oxo-1H-benzimidazol-1-yl)-1-piperidinyl]acetyl]-3a,4,5,9b-tetrahydro-7-methoxy-1H-benzo[e]indol-2-yl)-amine (0.500 g, 1.13 mmol) was carefully added in portions, with stirring, to a solution of lithium aluminum hydride (4.0 mmol) in tetrahydrofuran (20 mL). Considerable foaming occurred with each addition. The resultant mixture was heated at reflux for 1.5 hours. The resultant solution was cooled on an ice bath, and a solution of water (0.16 mL) in tetrahydrofuran (5 mL) was carefully added, with stirring, to the solution. With care, 15% aqueous sodium hydroxide (0.16 mL) was added followed by the addition of another aliquot of water (0.5 mL). The inorganic salts were removed by filtration and washed successively with tetrahydrofuran and dichloromethane. The organic solutions were combined, and the solvents were evaporated in vacuo. The residue was purified by preparative HPLC on a C18 reverse phase column eluted with a gradient of acetonitrile/water/trifluoroacetic acid from 10/90/0.1 (v/v) to 90/10/0.1 to give 2-[[4-(2,3-dihydro-2-oxo-1H-benzimidazol-1-yl)-1-piperidinyl]acetyl]-3a,4,5,9b-tetrahydro-7-methoxy-1H-benzo[e]indol-2-yl)-amine (12) as a trifluoroacetic acid salt, (0.166 g, 29%). MS m/z 430 (MH+); NMR(DMSO-d$_6$): δ 1.86–2.03 (m, 4 H), 2.58–2.83 (m, 4 H), 3.15–3.87 (m, 11 H), 4.33–4.45 (m, 1 H), 4.47–4.60 (m, 1 H), 6.94–7.04 (m, 3 H), 7.11–7.38 (m, 5 H), 10.03 (br s, 1 H), 10.41 (br s, 1 H) and 10.98 (br s, 1 H). (FIG. 6).

FIG. 6

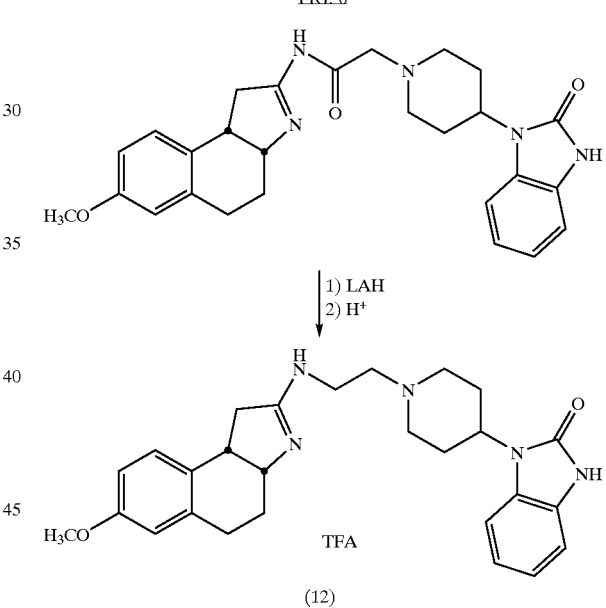

(12)

The following compounds of this invention were prepared from appropriately substituted β-tetralones as the starting material using the experimental protocols described above.

trans-4-[[(Phenylsulfonyl)amino]methyl]-N-(cis-3a,4,5,9b-tetrahydro-1H-benz[e]indol-2-yl)cyclohexanecarboxamide (13)

Calculated mass: 465; MS: 466 (M+H)$^+$

N-[[trans-4-[[(cis-3a,4,5,9b-tetrahydro-1 H-benz[e]indol-2-yl)amino]methyl]cyclohexyl]methyl]benzenesulfonamide (14)

Calculated mass: 451; MS: 452 (M+H)$^+$ trans-4-[[(Phenylsulfonyl)amino]methyl]-N-(cis-3a,4,5,9b-tetrahydro-7-fluoro-1H-benz[e]indol-2-yl)cyclohexanecarboxamide (15)

Calculated mass: 483; MS: 484 (M+H)$^+$

N-[[trans-4-[[(cis-3a,4,5,9b-tetrahydro-7-fluoro-1H-bnz[ ]indol-2-yl)amino]methyl]cyclohexyl]methyl]benzenesulfonamide (16)

Calculated mass: 469; MS: 470 (M+H)$^+$ trans-4-[[(Phenylsulfonyl)amino]methyl]-N-(cis-3a, 4,5,9b-tetrahydro-7chloro-1H-benz[e]indol-2-yl)cyclohexanecarboxamide (17)

Calculated mass: 499; MS: 500 (M+H)$^+$

N-[[trans-4-[[(cis-3a,4,5,9b-tetrahydro-7-chloro-1H-benz[e]indol-2-yl)amino]methyl]cyclohexyl]methyl]benzenesulfonamide (18)

Calculated mass: 485; MS: 486 (M+H)$^+$ trans-4-[[(Phenylsulfonyl)amino]methyl]-N-(cis-3a, 4,5,9b-tetrahydro-7-methoxy-1H-benz[e]indol-2-yl)cyclohexanecarboxamide (19)

Calculated mass: 513; MS: 514 (M+H)$^+$

2-[[4-(2,3-Dihydro-2-oxo-1H-benzimidazol-1-yl)-1-piperidinyl]acetyl]-[3a,4,5,9b-tetrahydro-7-methoxy-1H-benzo[e]indol-2-yl]-amine (20)

Calculated mass: 473; MS: 474 (M+H)$^+$

2-[[4-(2,3-Dihydro-2-oxo-1H-benzimidazol-1-yl)-1-piperidinyl]acetyl]-[3a,4,5,9b-tetrahydro-7-hydroxy-1H-benzo[e]indol-2-yl]-amine (21)

Calculated mass: 459; MS: 460 (M+H)$^+$

In vitro Assays
NPY5 HTS Centrifugation Assay

The compounds described in this invention were evaluated for binding to the human neuropeptide Y5 receptor.
Stable Transfection The human NPY5 receptor cDNA (Genbank Accession number U66275) was inserted into the vector pClneo (Invitrogen) and transfected into human embryonic kidney cells (HEK-293) via calcium phosphate method (Cullen 1987). Stably transfected cells were selected with G-418 (600 µg/mL). Stably transfected cells served as the source for the membranes for the NPY5 receptor binding assay.
Membrane Preparation NPY5-transfected HEK293 cells were grown to confluence in 150 cm$^2$ culture dishes. Cells were washed once with phosphate-buffered saline (Gibco Cat# 14040-133). Cells were then incubated in phosphate-buffered saline without calcium and without magnesium, supplemented with 2 mM EDTA. Cells were incubated for 10 minutes at room temperature and the cells were collected by repetitive pipeting. Cells were formed into pellets and then frozen at −80° C. until needed. Frozen pellets were homogenized with a polytron at full speed for 12 seconds in a homogenization buffer (20 mM Tris HCl, 5 mM EDTA, pH 7.4). Homogenates were centrifuged for 5 minutes at 4° C. at 200 g. Supernatants were transferred to corex tubes and centrifuged for 25 minutes at 28,000 g. Pellets were re-suspended in Binding (20 mM HEPES, 10 mM NaCl, 0.22 mM KH$_2$PO$_4$, 1.3 mM CaCl$_2$, 0.8 mM MgSO$_4$, pH 7.4). Membranes were kept on ice until use.

A competition binding assay, known to those skilled in the art, was used in which compounds of formula A compete with $^{125}$I-PYY for binding to cell membranes. In simple terms, the less $^{125}$I-PYY bound to the membranes implies that a compound is a good inhibitor (competitor). Bound $^{125}$I-PYY is determined by centrifugation of membranes, aspirating supernatant, washing away residual $^{125}$I-PYY and subsequently counting the bound sample in a gcounter.
Procedure for Radioligand Binding Assay Compounds to be tested were prepared as 10× stocks in binding buffer and added first to assay tubes (RIA vials, Sarstedt). Twenty (20) µL of each 10× compound stock is pipeted into vials and 80 µL of $^{125}$I-PYY (NEN catalog number NEX240), which has been diluted to a concentration of 200 pM in 0.25% BSA in binding buffer, is added to the compound tubes (final concentration of $^{125}$I-PYY is 80 pM). To each tube is added 100 µL of membranes and the mixture is agitated by pipeting 2 times. Samples are incubated for 1 hr at room temperature. Aluminum cast plates (Sarstedt) containing the vials are then centrifuged 10 minutes at 3200 rpm in a Sorvall RT6000. Supernatant is then aspirated. To each vial 400 µL PBS is added and this is then aspirated again. Vials are then put in carrier polypropylene 12×75 tube and counted in gamma counter (Packard). Non-specific binding is determined in the presence of 300 nM NPY. Percent inhibition of $^{125}$I-PYY binding is calculated by subtracting non-specific binding from the test samples (compound (I)), taking these counts and dividing by total binding, and multiplying by 100. Inhibitory concentration values (IC$_{50}$) of compounds that show appreciable inhibition of $^{125}$I-PYY binding are calculated by obtaining percent inhibition of $^{125}$I-PYY binding values at different concentrations of the test compound, and using a graphing program such as GraphPad Prism (San Diego, Calif.) to calculate the concentration of test compound that inhibits fifty-percent of $^{125}$I-PYY binding (Table 4).

Binding Affinities of Compounds of Formula A for the Human NPY Y5 Receptor (expressed as % Inhibition of $^{125}$I-PYY Binding)

TABLE 1

| # | % Inh @ 3 uM | % Inh @ 300 nM |
|---|---|---|
| 7 | 98 | 82 |
| 8 | 98 | 85 |
| 9 | 97 | 97 |
| 10 | 97 | 74 |
| 11 | 85 | 48 |
| 12 | 53 | 9 |
| 13 | 100 | 80 |
| 14 | 93 | 89 |
| 15 | 100 | 89 |
| 16 | 100 | 76 |
| 17 | 107 | 86 |
| 18 | 109 | 90 |
| 19 | 99 | 80 |
| 20 | 50 | 0 |
| 21 | 78 | 20 |

In vivo Assays
Rodent Feeding Model
Measurement of Food Intake in Food-Deprived Rats Male Long-Evans rats (180–200 grams) are housed individually and are maintained on once-a-day feeding schedule (i.e., 10 a.m. until 4 p.m.) for five days following quarantine to allow the animals to acclimate to feeding on powdered chow (#5002 PMI Certified Rodent Meal) during the allotted time. The chow is made available in a open jar, anchored in the cage by a wire, with a metal follower covering the food to minimize spillage. Water is available ad-libitum.

Animals are fasted for 18 hours prior to testing. At the end of the fasting period, animal are administered either compounds of the invention or vehicle. Vehicle and test compounds are administered either orally (5 mL/kg) 60 minutes prior to the experiment, or 30 minutes prior when given subcutaneously (1 mL/kg) or intraperitoneally (1 mL/kg). Compounds of the invention are administered orally as a suspension in aqueous 0.5% methylcellulose-0.4% Tween 80, or intraperitoneally as a solution or suspension in PEG 200; compound concentrations typically range from 1 mg/kg to 100 mg/kg, preferably from 10–30 mg/kg. Food intake is measured at 2, 4, and 6 hours after administration by weighing the special jar containing the food before the experiment and at the specified times. Upon completion of the experiment, all animals are given a one-week washout period before retesting.

Percent reduction of food consumption is calculated subtracting the grams of food consumed by the treated group from the grams of food consumed by the control group divided by the grams of food consumed by the control group, multiplied by 100. A negative value indicates a reduction in food consumption and a positive value indicates an increase in food consumption.

$$\% \text{ change} = \frac{\text{Treatment} - \text{Vehicle}}{\text{Vehicle}} \times 100$$

| Compound # | Dose (mg/kg) (# rats) | Food Consumption (avg. grams) | | | |
|---|---|---|---|---|---|
| | | 0–2 h (% chg.) | 0–4 h (% chg.) | 0–6 h (% chg.) | 2–6 h (% chg.) |
| Vehicle PEG-2000 | N = 8 | 10.19 g | 13.71 g | 21.03 g | 10.84 g |
| 10 | 30 (i.p.) N = 6 | 4.38 g (−57%) | 6.43 g (−53%) | 10.75 g (−49%) | 6.37 g (−41%) |
| Vehicle PEG-2000 | N = 8 | 9.13 g | 12.75 g | 21.25 g | 12.13 g |
| 8 | 10 (i.p.) N = 8 | 4.38 g (−52%) | 7.88 g (−38%) | 12.00 g (−43%) | 7.63 g (−37%) |

What is claimed is:

1. A compound of the formula:

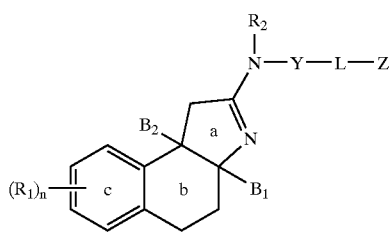

in which
R$_1$ is independently selected from the group consisting of hydrogen; hydroxy;
halo; C$_{1-8}$alkyl; C$_{1-8}$alkoxy; substituted C$_{1-8}$ alkyl wherein the substituent is halo; substituted C$_{1-8}$ alkoxy wherein the substituent is halo; trifluoroalkyl; C$_{1-8}$alkylthio and substituted C$_{1-8}$alkylthio wherein the substituent is selected from halo, trifluoroalkyl and C$_{1-8}$alkoxy; C$_{3-6}$cycloalkyl; C$_{3-8}$cycloalkoxy; nitro; amino; C$_{1-6}$alkylamino; C$_{1-8}$dialkylamino; C$_{4-8}$cycloalkylamino; cyano; carboxy; C$_{1-5}$alkylcarbonyloxy; C$_{1-5}$alkoxycarbonyloxy; formyl; carbamoyl; phenyl; and substituted phenyl wherein the substituent is selected from halo, hydroxyl, nitro, amino and cyano;

n is 0–2;

B$_2$ is selected from the group consisting of hydrogen; C$_{1-5}$alkyl; substituted C$_{1-5}$alkyl wherein the substituent is halo;

B$_2$ may have either a cis- or trans-stereochemical orientation with respect to B$_1$;

Y is methylene (—CH$_2$—) or carbonyl (C=O)

L is selected from the group consisting of C$_{1-8}$alkylene; C$_{2-10}$alkenylene; C$_{2-10}$alkynylene; C$_{3-7}$cycloalkylene; C$_{3-7}$cycloalkylC$_{1-4}$alkylene; arylC$_{1-4}$alkylene;

(N-methylene)piperidin-4-yl;

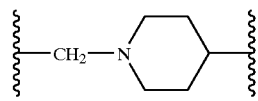

(N-methylene)piperazin-4-yl;

 and (N-methylene)piperidin-4,4-diyl;

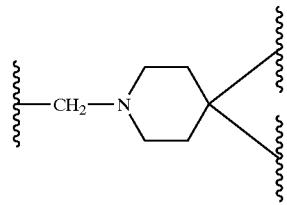

R$_2$ is independently selected from the group consisting of hydrogen; C$_{1-5}$alkyl; substituted C$_{1-5}$alkyl wherein the substituent is halo;

B$_1$ is hydrogen;

B$_2$ may have either a cis- or trans-stereochemical orientation with respect to B$_2$;

Z is selected from the group consisting of:

phenyl;

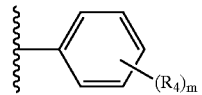

N-sulfonamido;

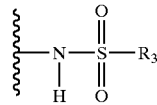

N-(aryl)sulfonamido;

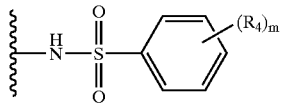

2,3-dihydro-2-oxo-1H-benzimidazol-1-yl;

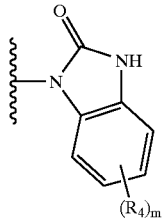

and 1-aryl-2,3-dihydro-4-oxo-imidazol-5,5-diyl;

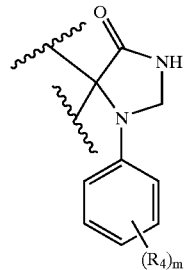

$R_3$ is selected from the group consisting of $C_{1-8}$alkyl; substituted $C_{1-8}$alkyl wherein the substituent is selected from alkoxy and halo; cycloalkyl; substituted cycloalkyl wherein the substituent is selected from $C_{1-8}$alkoxy and halo; naphthyl; substituted naphthyl wherein the substituent is selected from halo, nitro, amino and cyano; heteroaryl wherein the heteroaryl group is selected from pyridyl, pyrimidyl, furyl, thienyl and imidazolyl; and substituted heteroaryl wherein the substituent is selected from halo, nitro, amino and cyano;

$R_4$ is independently selected from the group consisting of $C_{1-8}$alkyl; alkoxy; hydroxy; halo; cyano, nitro; amino and alkylamino; substituted $C_{1-8}$alkyl wherein the substituent is halo;

m is 0–2;

with the following provisions:

when L is $C_{1-8}$alkylene; $C_{2-10}$alkenylene; $C_{2-10}$alkynylene; $C_{3-7}$cycloalkylene; $C_{3-7}$cycloalkylene$C_{1-4}$alkylene; aryl$C_{1-4}$alkylene; (N-methylene)piperidinA-4-yl;

then Z is phenyl; N-sulfonamido; N-(aryl)sulfonamido; or 2,3-dihydro-2-oxo-1H-benzimidazol-1-yl;

when L is (N-methylene)piperazin-4-yl;
then Z is phenyl or aryl; and when L is (N-methylene)piperidin-4,4,-diyl;
then Z is 1-aryl-2,3-dihydro-4-oxo-imidazol-5,5-diyl;

and enantiomers, diastereomers, and pharmaceutically acceptable salts thereof.

2. A compound of claim 1 wherein $R_1$ is hydrogen, alkyl, halo, alkoxy, hydroxy, nitro, amino or trifluoroalkyl;

$B_2$ and $B_1$ are hydrogen;

$R_2$ is hydrogen or alkyl;

Y is methylene or carbonyl;

L is alkylene, alkenylene, alkynylene, (N-methylene)piperidin-4-yl, (N-methylene)piperazin-4-yl or (N-methylene)piperidin-4,4-diyl;

Z is phenyl, N-sulfonamido, N(aryl)sulfonamido, 2,3-dihydro-2-oxo-1H-benzimidazol-1-yl or 1-aryl-2,3-dihydro-oxo-imidazol-5,5-diyl;

$R_3$ is alkyl, substituted alkyl, cycloalkyl, aryl, substituted aryl, heteroaryl or substituted heteroaryl;

$R_4$ is alkyl, alkoxy, hydroxy, halo, cyano, nitro, amino, alkylamino or substituted alkyl;

n is 0–2;

m is 0–2;

provided that when:

L is $C_{1-8}$alkylene, $C_{2-10}$alkenylene; $C_{2-10}$alkynylene, $C_{3-7}$cycloalkylene, $C_{3-7}$cycloalkylene$C_{1-4}$alkylene, aryl$C_{1-4}$alkylene or (N-methylene)piperidin-4-yl, then Z is phenyl, N-sulfonamido, N-(aryl)sulfonamido or 2,3-dihydro-2-oxo-1H-benzimidazol-1 -yl;

when L is (N-methylene)piperazin-4-yl, then Z is phenyl; and when L is (N-methylene)piperidin-4,4-diyl, then Z is 1-aryl-2,3-dihydro-4-oxo-imidazol-5,5-diyl;

and the enantiomers, diastereomers and pharmaceutically acceptable salts thereof.

3. A compound of claim 1 selected form the group consisting of:

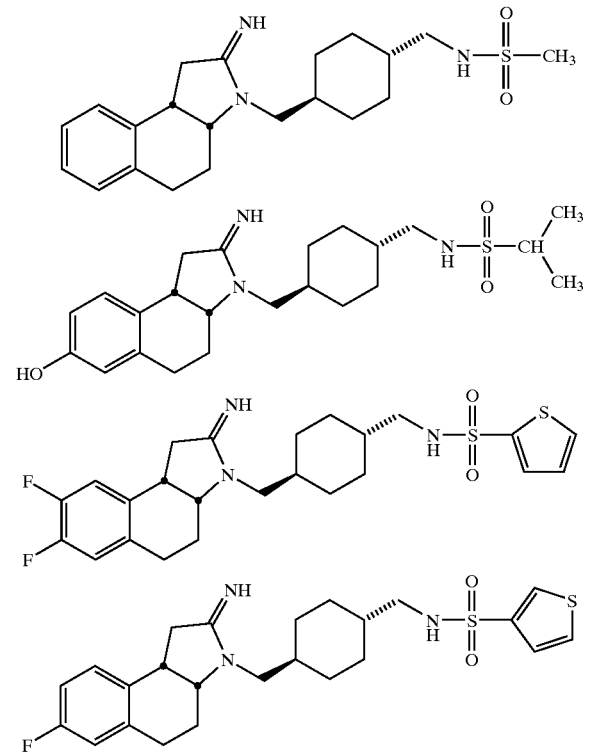

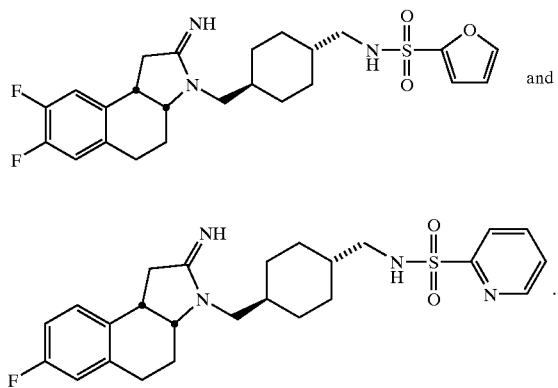
and
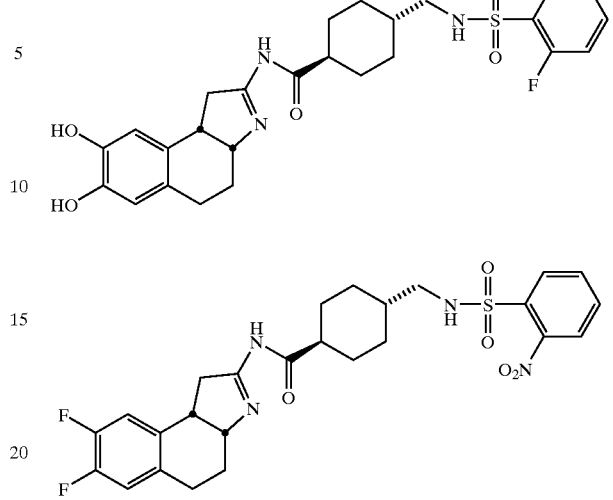
4. A compound of claim 1 selected from the group consisting of:
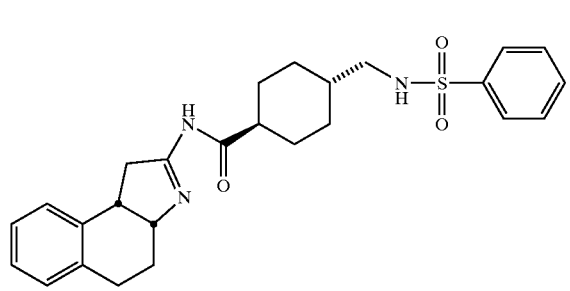
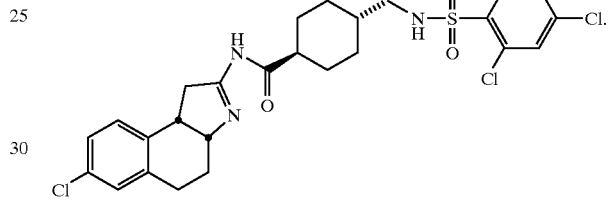
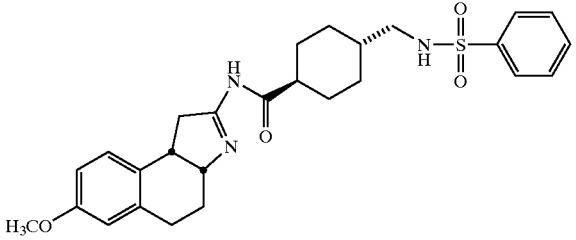
5. A compound of claim 1 selected from the group consisting of:
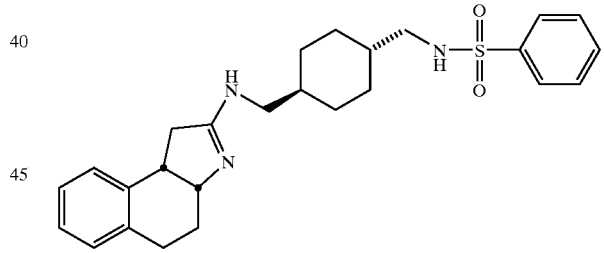
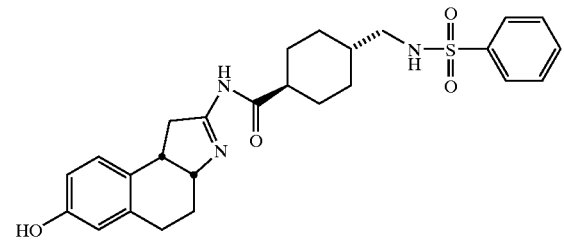
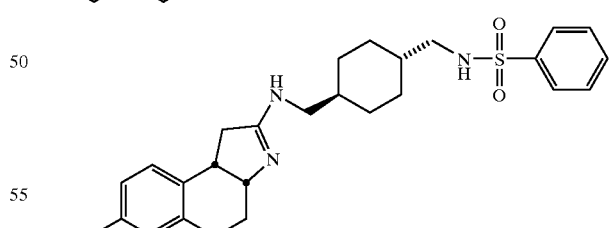
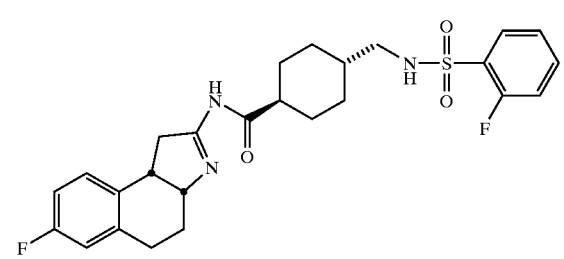
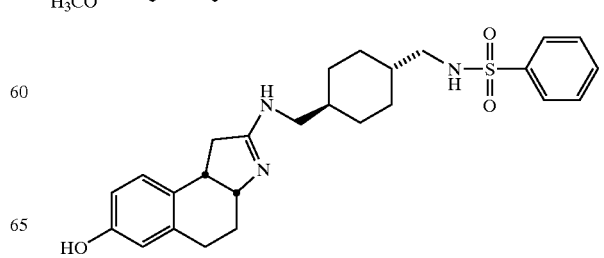

-continued
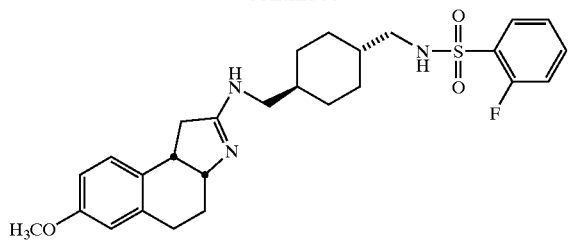
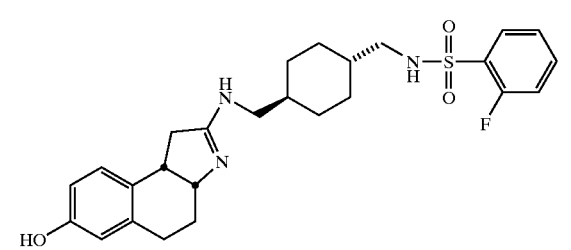
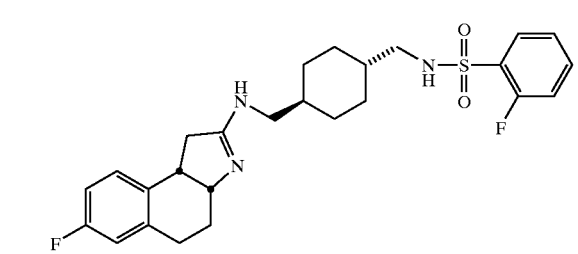
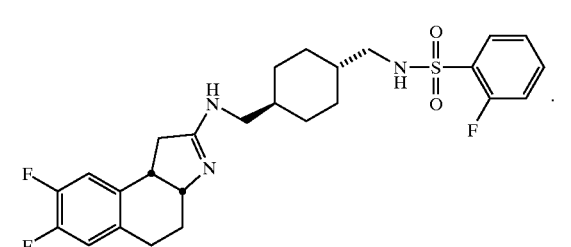
6. A compound of claim 1 selected from the group consisting of:
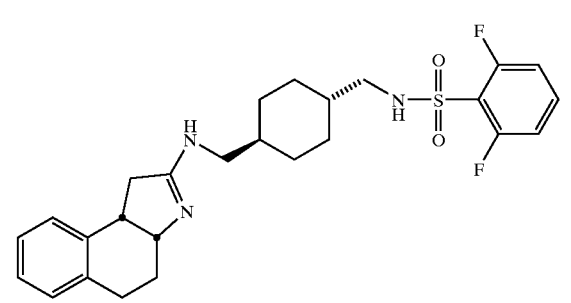
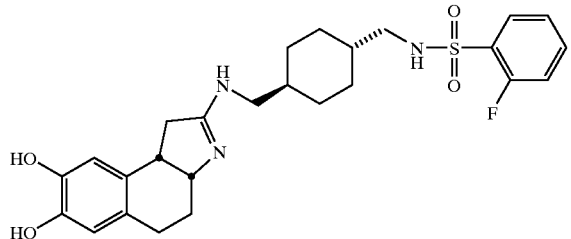
-continued
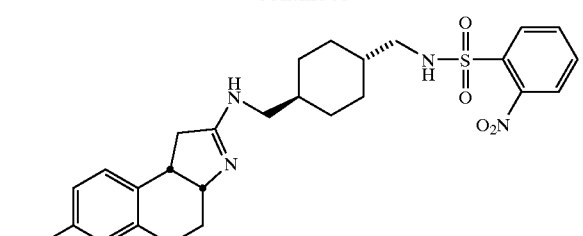
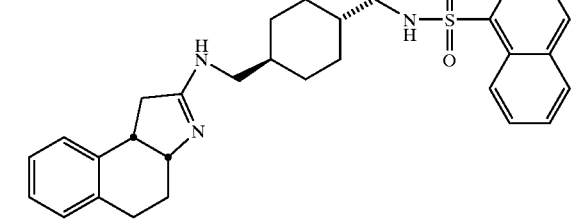
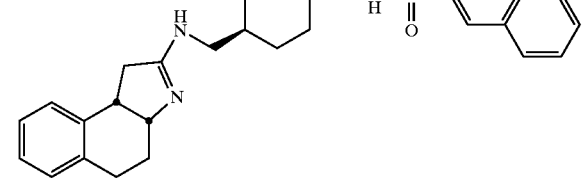
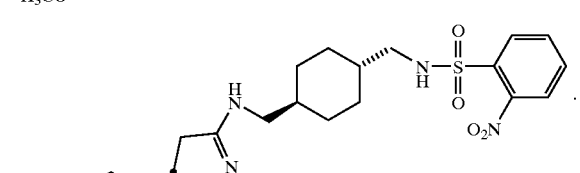
7. A compound of claim 1 selected from the group consisting of:
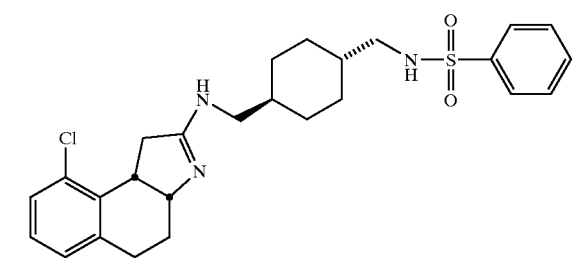

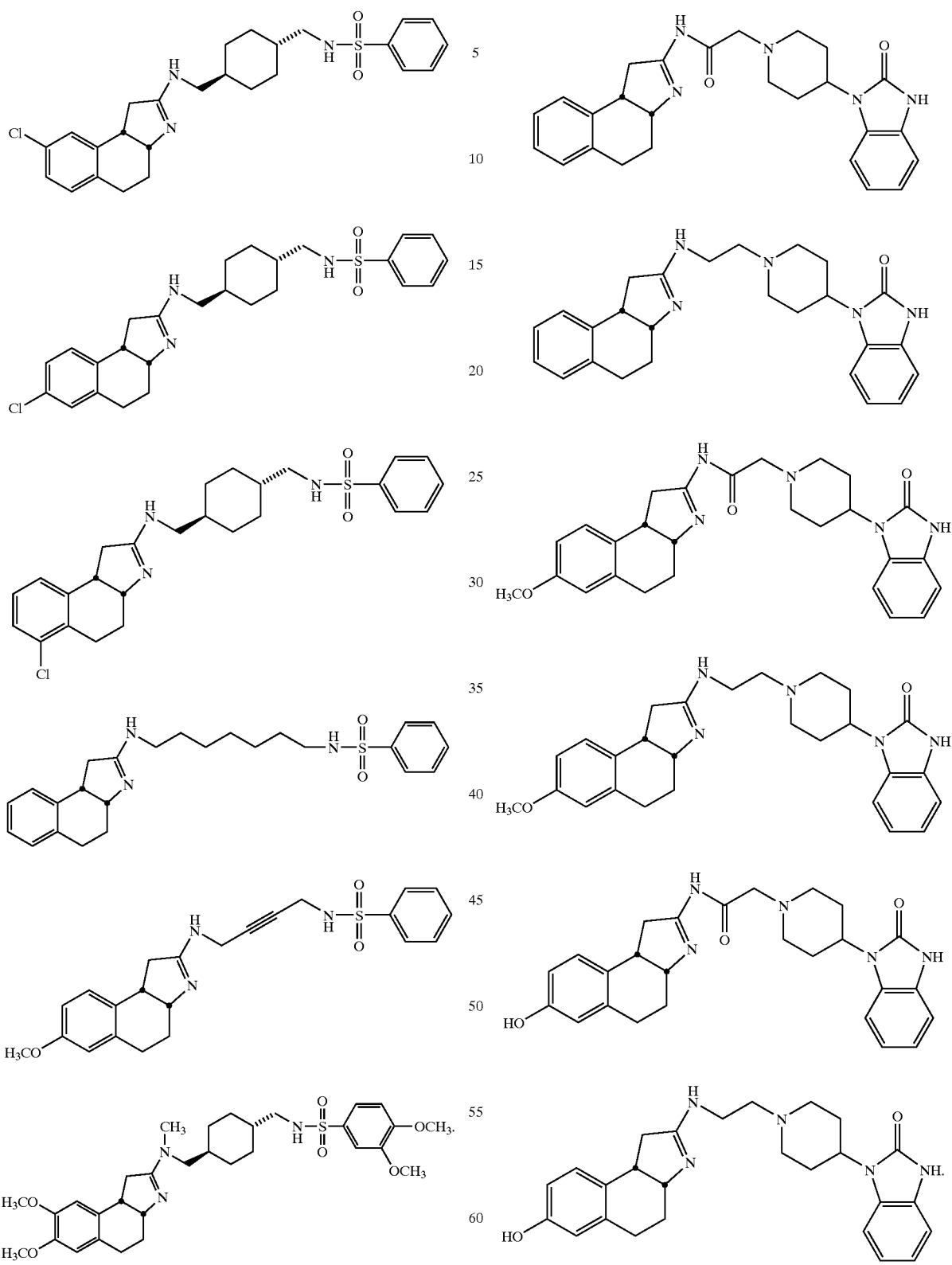
8. A compound of claim 1 selected from the group consisting of:
9. A compound of claim 1 selected from the group consisting of:

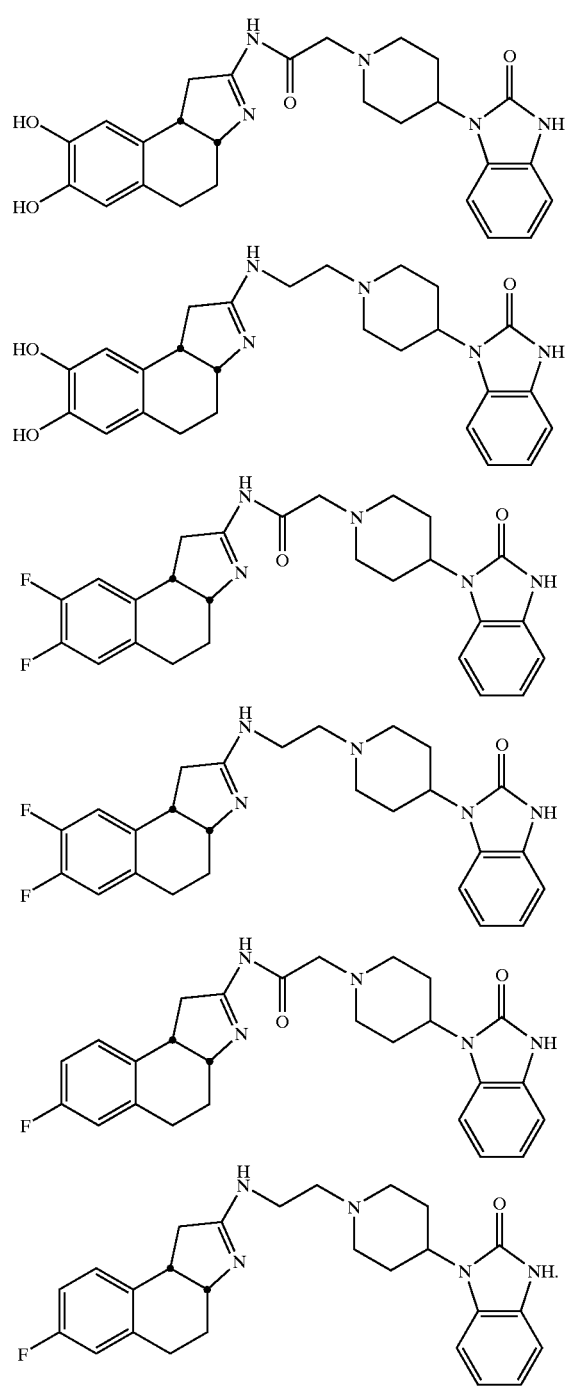
10. A compound of claim 1 selected from the group consisting of:
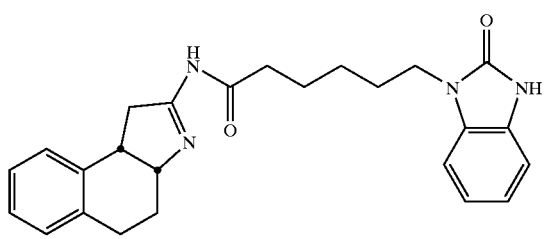
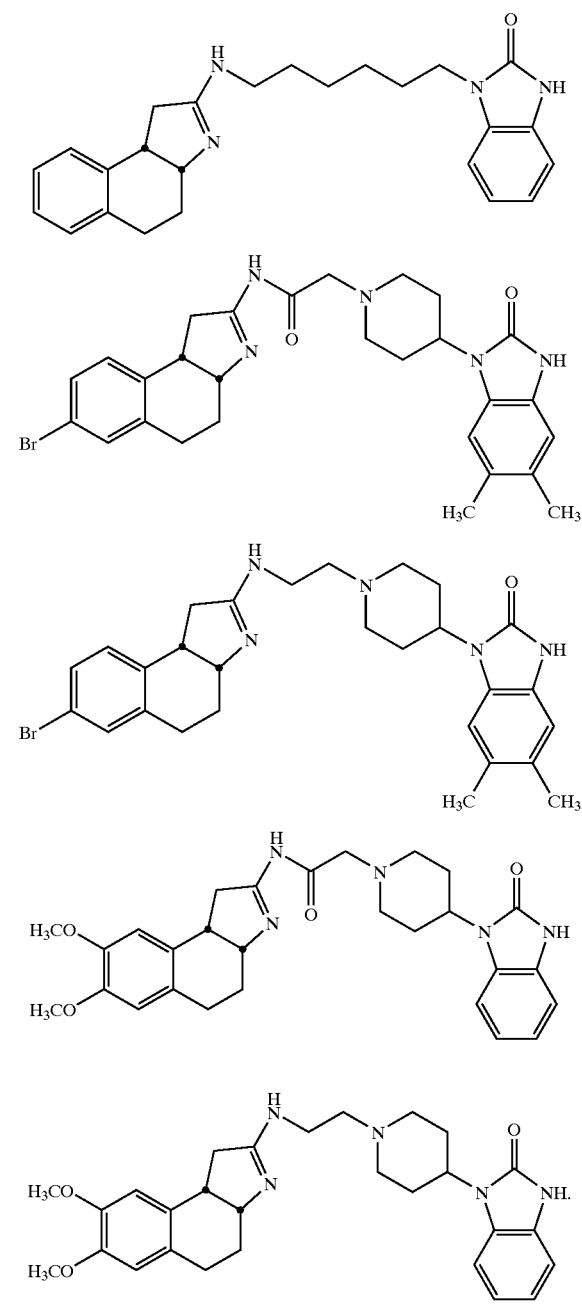
11. A compound of claim 1 selected from the group consisting of:
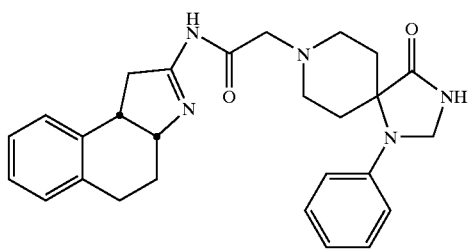

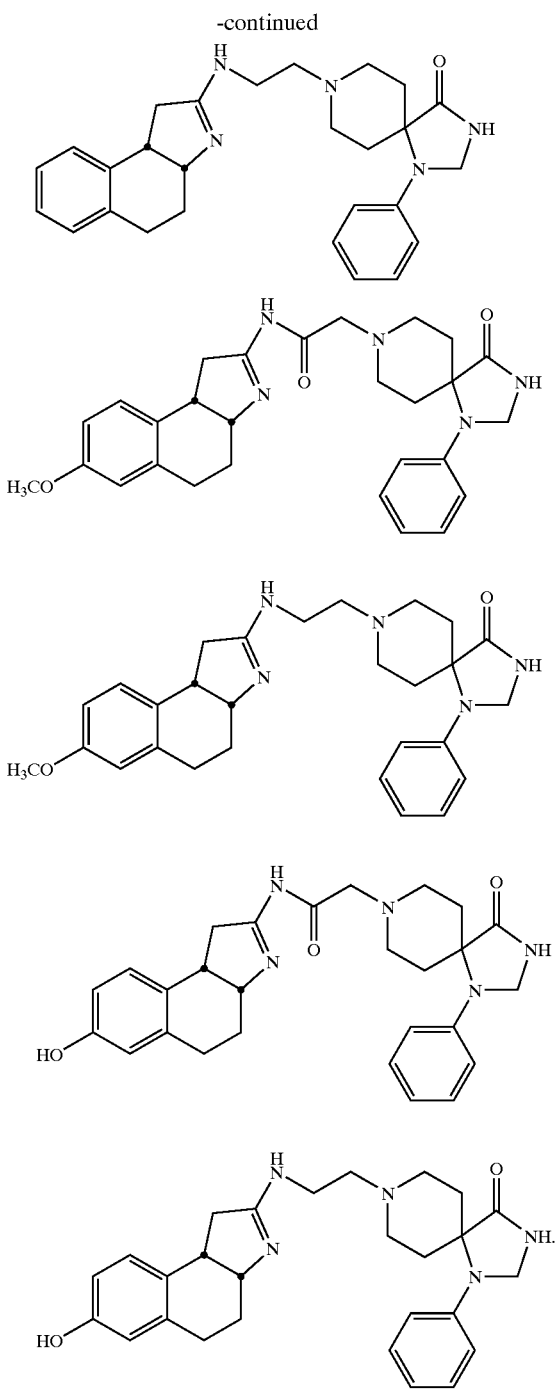
12. A compound of claim 1 selected from the group consisting of:
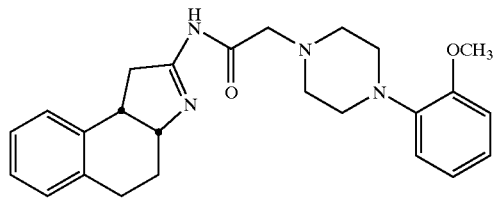
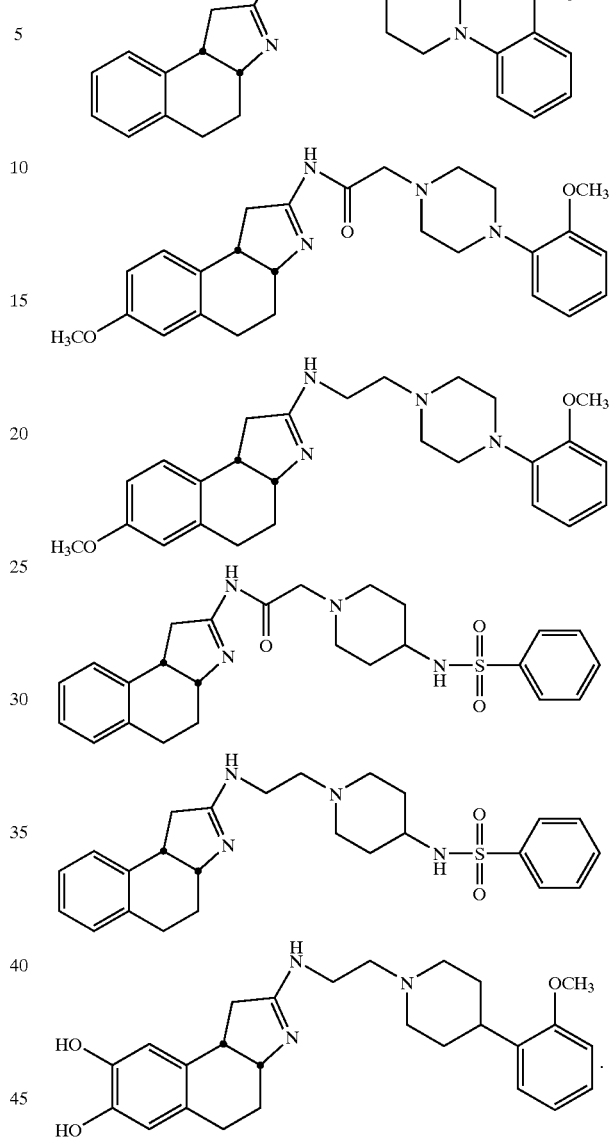
13. A compound of claim 1 selected from the group consisting of:
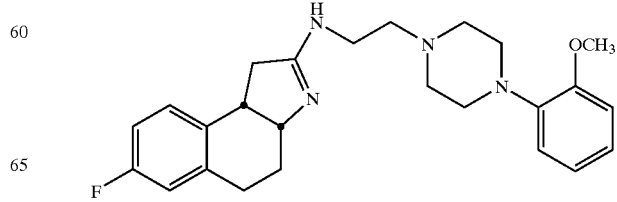

14. A compound of claim 1 selected from the group consisting of:

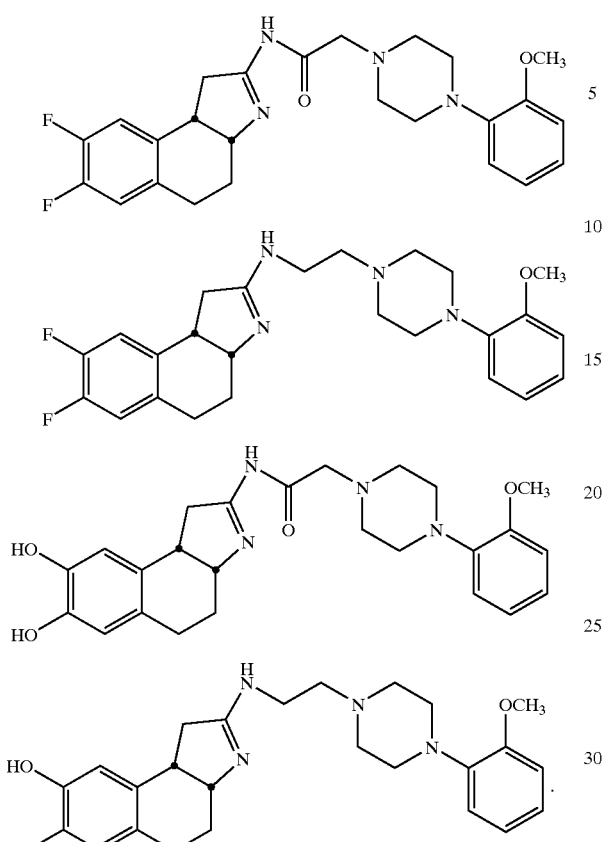

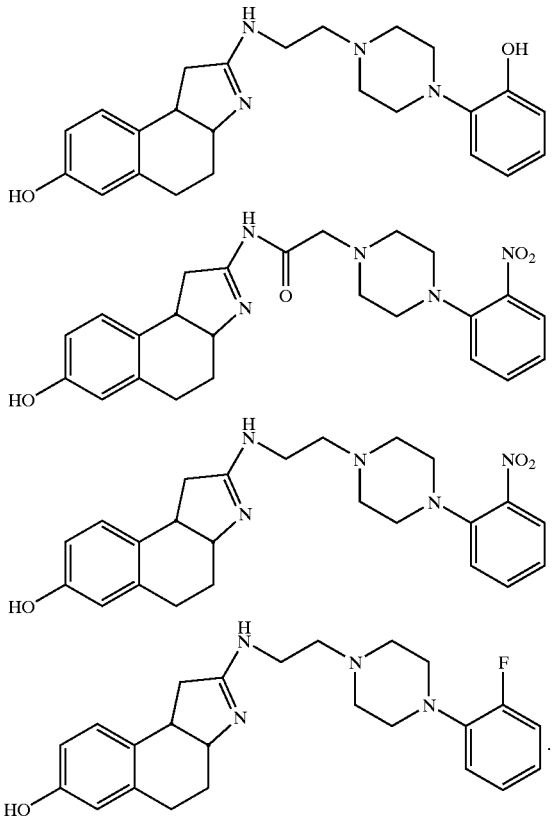

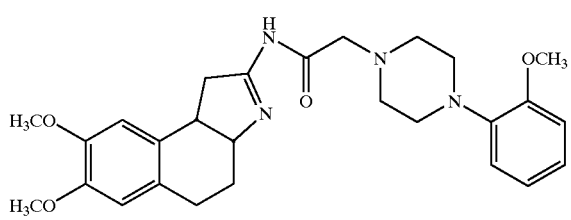

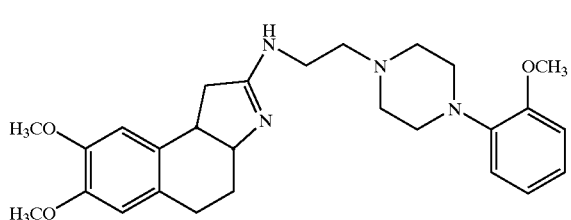

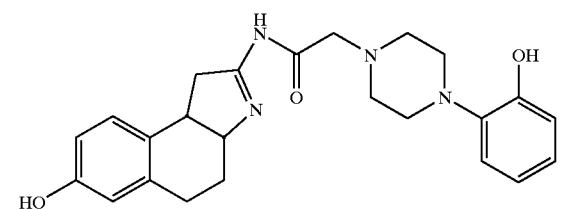

15. A compound of claim 1 wherein:

$R_1$ is hydrogen, alkyl, halo, alkoxy, hydroxy, nitro, amino or trifluoroalkyl;

$B_2$ and $B_1$ are hydrogen;

$R_2$ is hydrogen or alkyl;

Y is methylene or carbonyl;

L is selected from the group consisting of $C_{1-8}$alkylene; $C_{2-10}$alkenylene; $C_{2-10}$alkynylene; $C_{3-7}$cycloalkylene; $C_{3-7}$cycloalkyl$C_{1-4}$alkylene; aryl$C_{1-4}$alkylene; (N-methylene)piperidin-4-yl, (N-methylene)piperazin-4-yl and (N-methylene)piperidin-4,4-diyl;

Z is phenyl, N-sulfonamido, N(aryl)sulfonamido, 2,3-dihydro-2-oxo-1H-benzimidazol-1-yl or 1-aryl-2,3-dihydro-4-oxo-imidazol-5,5-diyl;

$R_3$ is alkyl, substituted alkyl, cycloalkyl, aryl, substituted aryl, heteroaryl or substituted heteroaryl;

$R_4$ is independently selected from the group consisting of $C_{1-8}$alkyl; alkoxy; hydroxy; halogen; cyano, nitro; amino; alkylamino; and substituted $C_{1-8}$alkyl wherein the substituent is halo;

n is 0–2;

m is 0–2;

provided that when:

L is $C_{1-8}$alkylene, $C_{2-10}$alkenylene; $C_{2-10}$alkynylene, $C_{3-7}$cycloalkylene, $C_{3-7}$cycloalkylene$C_{1-4}$alkylene, aryl$C_{1-4}$alkylene or (N-methylene)piperidin-4-yl, then Z is phenyl, N-sulfonamido, N-(aryl)sulfonamido or 2,3-dihydro-2-oxo-1H-benzimidazol-1-yl;

when L is (N-methylene)piperazin-4-yl, then Z is phenyl; and when

L is (N-methylene)piperidin-4,4-diyl, then Z is 1-aryl-2,3-dihydro-4-oxo-imidazol-5,5-diyl;
and the enantiomers, diastereomers and pharmaceutically acceptable salts thereof.

16. A method of treating disorders and diseases associated with NPY receptor subtype Y5 comprising administering to a mammal in need of such treatment a therapeutically effective amount of a compound of claim 1 selected from the group consisting of eating disorders, obesity, anorexia nervosa, bulimia nervosa, diabetes, dyspilipidimia, hypertension, memory loss, epileptic seizures, migraine, sleep disorders, pain, sexual/reproductive disorders, depression and anxiety.

17. A pharmaceutical composition according to claim 16 for the treatment of disorders or disease states caused by eating disorders, obesity, anorexia nervosa, bulimia nervosa, diabetes, dyspilipidimia, hypertension, memory loss, epileptic seizures, migraine, sleep disorders, pain, sexual/reproductive disorders, depression or anxiety.

* * * * *